US008106039B2

(12) United States Patent
Meggers et al.

(10) Patent No.: US 8,106,039 B2
(45) Date of Patent: Jan. 31, 2012

(54) METAL COMPLEX PHOSPHATIDYL-INOSITOL-3-KINASE INHIBITORS

(75) Inventors: Eric Meggers, Philadelphia, PA (US); Peng Xie, Philadelphia, PA (US); Douglas S. Williams, Philadelphia, PA (US); Ronen Marmorstein, Swarthmore, PA (US)

(73) Assignees: The Trustees Of The University Of Pennsylvania, Philadelphia, PA (US); The Wistar Institute Of Anatomy And Biology, Philadelphia, PA (US)

( * ) Notice: Subject to any disclaimer, the term of this patent is extended or adjusted under 35 U.S.C. 154(b) by 941 days.

(21) Appl. No.: 12/112,748

(22) Filed: Apr. 30, 2008

(65) Prior Publication Data

US 2009/0275547 A1 Nov. 5, 2009

(51) Int. Cl.
*A61K 31/555* (2006.01)
*C07F 15/00* (2006.01)
(52) U.S. Cl. .......................................... 514/185; 546/10
(58) Field of Classification Search .................... 546/10; 514/185
See application file for complete search history.

(56) References Cited

U.S. PATENT DOCUMENTS

| | | | |
|---|---|---|---|
| 6,451,838 B1 | 9/2002 | Moon et al. | |
| 6,555,539 B2 | 4/2003 | Reich et al. | |
| 6,593,357 B1 | 7/2003 | Green et al. | |
| 6,613,776 B2 | 9/2003 | Knegtel et al. | |
| 2005/0171076 A1 | 8/2005 | Meggers et al. | |
| 2006/0019942 A1 | 1/2006 | Meggers et al. | |

OTHER PUBLICATIONS

"Remington's Pharmaceutical Sciences", 18th Edition, Chapter 86, pp. 1581-1595, Mack Publishing Company, 1990.
Atilla-Gokcumen, G. E., Williams, D. S., Bregman, H., Pagano, N., and Meggers, E. (2006) Organometallic compounds with biological activity: a very selective and highly potent cellular inhibitor for glycogen synthase kinase 3, Chembiochem 7, 1443-1450.
Baggiolini, M., Dewald, B., Schnyder, J., Ruch, W., Cooper, P. H., and Payne, T. G. (1987) Inhibition of the phagocytosis-induced respiratory burst by the fungal metabolite wortmannin and some analogues, Exp Cell Res 169, 408-418.
Benistant, C., Chapuis, H., and Roche, S. (2000) A specific function for phosphatidylinositol 3-kinase alpha (p85alpha-p110alpha) in cell survival and for phosphatidylinositol 3-kinase beta (p85alpha-p110beta) in de novo DNA synthesis of human colon carcinoma cells, Oncogene 19, 5083-5090.
Bregman, H., and Meggers, E. (2006) Ruthenium half-sandwich complexes as protein kinase inhibitors: an N-succinimidyl ester for rapid derivatizations of the cyclopentadienyl moiety, Org Lett 8, 5465-5468.

Bregman, H., Carroll, P. J., and Meggers, E. (2006) Rapid access to unexplored chemical space by ligand scanning around a ruthenium center: discovery of potent and selective protein kinase inhibitors, J Am Chem Soc 128, 877-884.
Bregman, H., Williams, D. S., Atilla, G. E., Carroll, P. J., and Meggers, E. (2004) An organometallic inhibitor for glycogen synthase kinase 3, J Am Chem Soc 126, 13594-13595.
Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T., and Warren, G. L. (1998) Crystallography & NMR system: A new software suite for macromolecular structure determination., Acta Crystallogr D Biol Crystallogr 54, 905-921.
Camps, M., Ruckle, T., Ji, H., Ardissone, V., Rintelen, F., Shaw, J., Ferrandi, C., Chabert, C., Gillieron, C., Francon, B., Martin, T., Gretener, D., Perrin, D., Leroy, D., Vitte, P. A., Hirsch, E., Wymann, M. P., Cirillo, R., Schwarz, M. K., and Rommel, C. (2005) Blockade of PI3Kgamma suppresses joint inflammation and damage in mouse models of rheumatoid arthritis, Nat Med 11, 936-943.
Collaborative Computational Project, N. (1994) The CCP4 suite: programs for protein crystallography, Acta Crystallogr D Biol Crystallogr 50, 760-763.
Davies, S. P., Reddy, H., Caivano, M., and Cohen, P. (2000) Specificity and mechanism of action of some commonly used protein kinase inhibitors, Biochem J 351, 95-105.
Debreczeni, J. E., Bullock, A. N., Atilla, G. E., Williams, D. S., Bregman, H., Knapp, S., and Meggers, E. (2006) Ruthenium half-sandwich complexes bound to protein kinase Pim-1, Angew Chem Int Ed Engl 45, 1580-1585.
Domin, J., and Waterfield, M. D. (1997) Using structure to define the function of phosphoinositide 3-kinase family members, FEBS Lett 410, 91-95.
Emsley, P., and Cowtan, K. (2004) Coot: Model-Building Tools for Molecular Graphics, Acta Crystallogr. D 60, 2126-2132.
Fruman, D. A., Meyers, R. E., and Cantley, L. C. (1998) Phosphoinositide kinases, Annu Rev Biochem 67, 481-507.
Gouet, P., Robert, X., and Courcelle, E. (2003) ESPript/ENDscript: Extracting and rendering sequence and 3D information from atomic structures of proteins, Nucleic Acids Res 31, 3320-3323.
Hickey, F. B., and Cotter, T. G. (2006) BCR-ABL regulates phosphatidylinositol 3-kinase-p110gamma transcription and activation and is required for proliferation and drug resistance, J Biol Chem 281, 2441-2450.
Huang, C. H., Mandelker, D., Schmidt-Kittler, O., Samuels, Y., Velculescu, V. E., Kinzler, K. W., Vogelstein, B., Gabelli, S. B., and Amzel, L. M. (2007) The structure of a human p110alpha/p85alpha complex elucidates the effects of oncogenic PI3Kalpha mutations, Science 318, 1744-1748.
Jacobs, M. D., Black, J., Futer, O., Swenson, L., Hare, B., Fleming, M., and Saxena, K. (2005) Pim-1 ligand-bound structures reveal the mechanism of serine/threonine kinase inhibition by LY294002, J Biol Chem 280, 13728-13734.

(Continued)

*Primary Examiner* — Charanjit Aulakh
(74) *Attorney, Agent, or Firm* — Woodcock Washburn, LLP

(57) ABSTRACT

Provided are novel organometallic compounds that inhibit PI3K lipid kinase and phospho-AKT in human melanoma cells, and also inhibit the migration of melanoma cells. The present invention is also directed to methods for inhibiting cancer cell proliferation, migration or both comprising contacting a cancer cell with a disclosed organometallic kinase inhibitor. Also disclosed are methods for treating a kinase-affected disease or condition comprising administering to a subject in need thereof a therapeutically effective amount of a disclosed organometallic kinase inhibitor.

21 Claims, 16 Drawing Sheets

OTHER PUBLICATIONS

Jones, T. A., Zou, J. Y., Cowan, S. W., and Kjeldgaard, M. (1991) Improved methods for building protein models in electron density maps and the location of errors in these models, Acta Crystallogr. A 47, 110-119.

Knight, Z. A., Chiang, G. G., Alaimo, P. J., Kenski, D. M., Ho, C. B., Coan, K., Abraham, R. T., and Shokat, K. M. (2004) Isoform-specific phosphoinositide 3-kinase inhibitors from an arylmorpholine scaffold, Bioorg Med Chem 12, 4749-4759.

Knight, Z. A., Gonzalez, B., Feldman, M. E., Zunder, E. R., Goldenberg, D. D., Williams, O., Loewith, R., Stokoe, D., Balla, A., Toth, B., Balla, T., Weiss, W. A., Williams, R. L., and Shokat, K. M. (2006) A pharmacological map of the PI3-K family defines a role for p110alpha in insulin signaling, Cell 125, 733-747.

Krissinel, E., and Henrick, K. (2004) Secondary-structure matching (SSM), a new tool for fast protein structure alignment in three dimensions, Acta Crystallogr D Biol Crystallogr 60, 2256-2268.

Meggers, E. (2007) Exploring biologically relevant chemical space with metal complexes, Curr Opin Chem Biol 11, 287-292.

Meggers, E., Atilla-Gokcumen, G. E., Bregman, H., Maksimoska, J., Mulcahy, S. P., Pagano, N., and Williams, D. S. (2007) Synlett eFirst.

Mizoguchi, M., Nutt, C. L., Mohapatra, G., and Louis, D. N. (2004) Genetic alterations of phosphoinositide 3-kinase subunit genes in human glioblastomas, Brain Pathol 14, 372-377.

Pagano, N., Maksimoska, J., Bregman, H., Williams, D. S., Webster, R. D., Xue, F., and Meggers, E. (2007) Ruthenium half-sandwich complexes as protein kinase inhibitors: derivatization of the pyridocarbazole pharmacophore ligand, Org Biomol Chem 5, 1218-1227.

Rodriguez-Viciana, P., Warne, P. H., Dhand, R., Vanhaesebroeck, B., Gout, I., Fry, M. J., Waterfield, M. D., and Downward, J. (1994) Phosphatidylinositol-3-OH kinase as a direct target of Ras, Nature 370, 527-532.

Rommel, C., Camps, M., and Ji, H. (2007) PI3K delta and PI3K gamma: partners in crime in inflammation in rheumatoid arthritis and beyond?, Nat Rev Immunol 7, 191-201.

Samuels, Y., Diaz, L. A., Jr., Schmidt-Kittler, O., Cummins, J. M., Delong, L., Cheong, I., Rago, C., Huso, D. L., Lengauer, C., Kinzler, K. W., Vogelstein, B., and Velculescu, V. E. (2005) Mutant PIK3CA promotes cell growth and invasion of human cancer cells, Cancer Cell 7, 561-573.

Samuels, Y., Wang, Z., Bardelli, A., Silliman, N., Ptak, J., Szabo, S., Yan, H., Gazdar, A., Powell, S. M., Riggins, G. J., Willson, J. K., Markowitz, S., Kinzler, K. W., Vogelstein, B., and Velculescu, V. E. (2004) High frequency of mutations of the PIK3CA gene in human cancers, Science 304, 554.

Smalley, K. S. M., Brafford, P., Haass, N. K., Brandner, J. M., Brown, E., and Herlyn, M. (2005) Up-regulated expression of zonula occludens protein-1 in human melanoma associates with N-cadherin and contributes to invasion and adhesion, American Journal of Pathology 166, 1541-1554.

Smalley, K. S., and Herlyn, M. (2005) Targeting intracellular signaling pathways as a novel strategy in melanoma therapeutics, Ann N Y Acad Sci 1059, 16-25.

Smalley, K. S., Contractor, R., Haass, N. K., Kulp, A. N., Atilla-Gokcumen, G. E., Williams, D. S., Bregman, H., Flaherty, K. T., Soengas, M. S., Meggers, E., and Herlyn, M. (2007) An organometallic protein kinase inhibitor pharmacologically activates p53 and induces apoptosis in human melanoma cells, Cancer Res 67, 209-217.

Smalley, K. S., Haass, N. K., Brafford, P. A., Lioni, M., Flaherty, K. T., and Herlyn, M. (2006) Multiple signaling pathways must be targeted to overcome drug resistance in cell lines derived from melanoma metastases, Mol Cancer Ther 5, 1136-1144.

Stahl, J. M., Sharma, A., Cheung, M., Zimmerman, M., Cheng, J. Q., Bosenberg, M. W., Kester, M., Sandirasegarane, L., and Robertson, G. P. (2004) Deregulated Akt3 activity promotes development of malignant melanoma, Cancer Res 64, 7002-7010.

Sugimoto, Y., Whitman, M., Cantley, L. C., and Erikson, R. L. (1984) Evidence that the Rous sarcoma virus transforming gene product phosphorylates phosphatidylinositol and diacylglycerol, Proc Natl Acad Sci U S A 81, 2117-2121.

Vagin, A., and Teplyakov, A. (1997) MOLREP: An automated program for molecular replacement, J Appl Cryst 30, 1022-1025.

Vanhaesebroeck, B., and Waterfield, M. D. (1999) Signaling by distinct classes of phosphoinositide 3-kinases, Exp Cell Res 253, 239-254.

Vivanco, I., and Sawyers, C. L. (2002) The phosphatidylinositol 3-Kinase AKT pathway in human cancer, Nat Rev Cancer 2, 489-501.

Vlahos, C. J., Matter, W. F., Hui, K. Y., and Brown, R. F. (1994) A specific inhibitor of phosphatidylinositol 3-kinase, 2-(4-morpholinyl)-8-phenyl-4H-1-benzopyran-4-one (LY294002), J Biol Chem 269, 5241-5248.

Vogt, P. K., Kang, S., Elsliger, M. A., and Gymnopoulos, M. (2007) Cancer-specific mutations in phosphatidylinositol 3-kinase, Trends Biochem Sci 32, 342-349.

Walker, E. H., Pacold, M. E., Perisic, O., Stephens, L., Hawkins, P. T., Wymann, M. P., and Williams, R. L. (2000) Structural determinants of phosphoinositide 3-kinase inhibition by wortmannin, LY294002, quercetin, myricetin, and staurosporine, Mol Cell 6, 909-919.

Walker, E. H., Perisic, O., Ried, C., Stephens, L., and Williams, R. L. (1999) Structural insights into phosphoinositide 3-kinase catalysis and signalling, Nature 402, 313-320.

Whitman, M., Kaplan, D. R., Schaffhausen, B., Cantley, L., and Roberts, T. M. (1985) Association of phosphatidylinositol kinase activity with polyoma middle-T competent for transformation, Nature 315, 239-242.

Williams, D. S. et al, (2005) Switching on a signaling pathway with an organoruthenium complex, Angew Chem Int Ed Engl 44, 1984-1987.

Williams, D. S., Carroll, P. J., and Meggers, E. (2007) Platinum complex as a nanomolar protein kinase inhibitor, Inorg Chem 46, 2944-2946.

Xie, P. et al., "Structure-Based Design of an Organoruthenium Phosphatidyl-inositol-3-kinase Inhibitor Reveals a Switch Governing Lipid Kinase Potency and Selectivity," ACS Chem Biol., May 16, 2008, 3(5), 305-316.

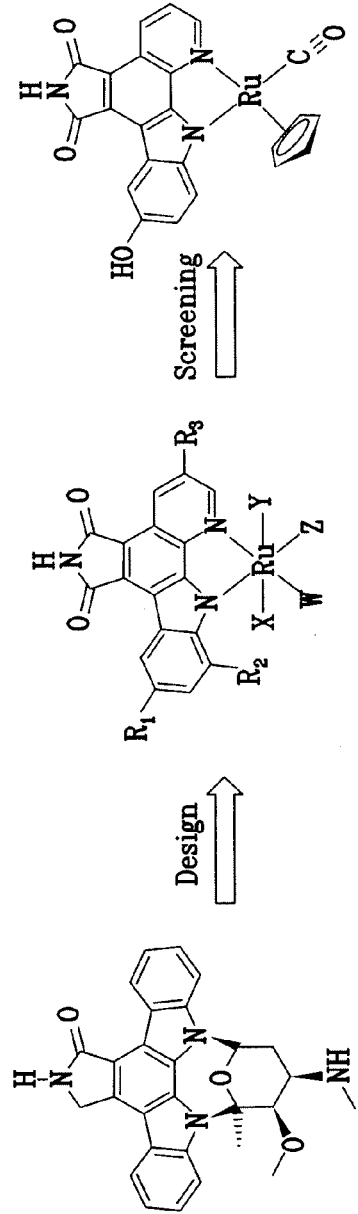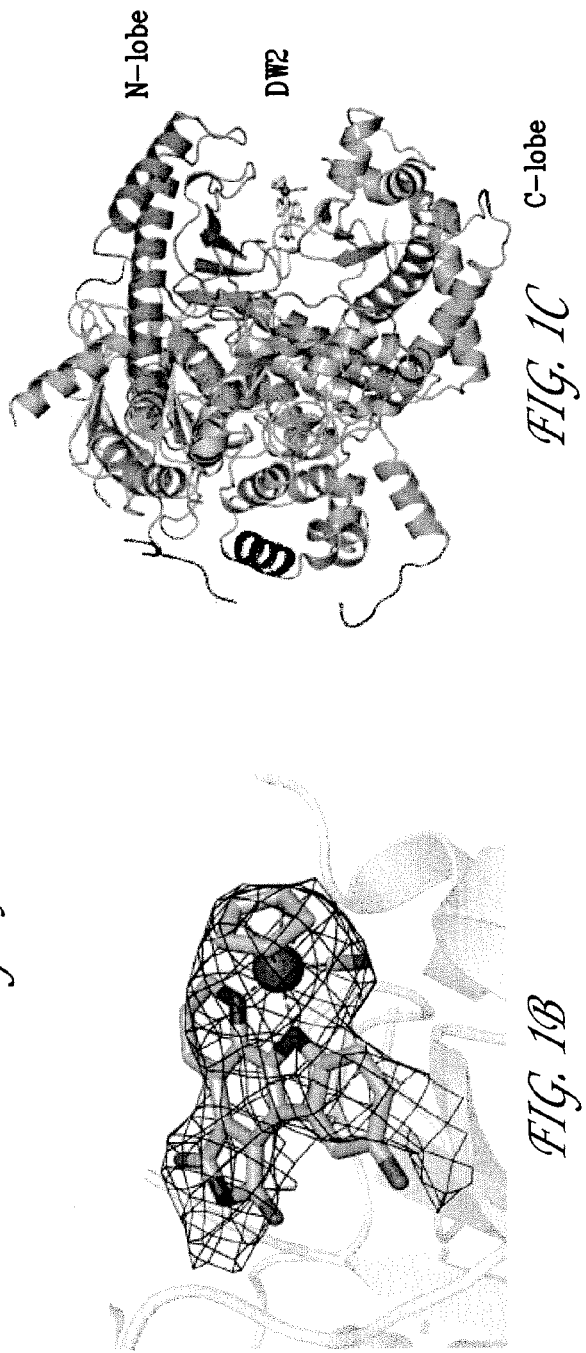
FIG. 1A  FIG. 1B  FIG. 1C

| | R1 | R2 | R3 | R4 | IC50 (μM) PI3Kγ | GSK3β |
|---|---|---|---|---|---|---|
| HB12 | H | H | H | H | >>1[a] | 0.05 |
| DW12 | H | OH | H | H | 0.75 | 0.0014 |
| DW12Me | CH3 | OH | H | H | 0.5 | >1 |
| EAd125 | CH3 | OH | F | H | 0.18 | 0.7 |
| E5 | CH3 | OH | F | X | 0.04 | 4 |

[a] 100% PI3K activity at 1 μM of HB12

FIG. 10C

METAL COMPLEX PHOSPHATIDYL-INOSITOL-3-KINASE INHIBITORS

STATEMENT OF GOVERNMENT RIGHTS

Research leading to the disclosed inventions was funded, in part, by the U.S. National Institutes of Health, Grant No. R01 GM071695 (Eric Meggers). Accordingly, the United States Government may have rights in the inventions described herein.

FIELD OF THE INVENTION

The present application pertains to metal complex protein kinases inhibitors, methods for making such compounds, and methods for using such compounds for treating diseases and disorders mediated by kinase activity.

BACKGROUND OF THE INVENTION

The development of small molecules that perturb specific protein functions is of great importance for probing biological processes and ultimately for the development of potent and safe drugs. Medicinal chemistry is predominately focused on the design of organic molecules, whereas the incorporation of inorganic components into drugs is much less investigated. Furthermore, in almost all metallopharmaceuticals, the metal ion possesses a reactive feature. We have found that certain organometallic and inorganic compounds are useful as structural scaffolds for enzyme inhibition. Such metal-ligand assemblies allow convergent synthetic approaches and give access to structural motifs that differ from purely organic molecules. Nature makes extended use of metals not only for their reactivity but also for structural purposes, as for example in zinc binding aspartate transcarbamoylase and zinc finger domains, or the calcium binding protein calmodulin.

Protein kinases regulate most aspects of cellular life and are one of the main drug targets. An example is the microbial alkaloid staurosporine, which is a very potent, but relatively nonspecific inhibitor of many protein kinases. Many staurosporine derivatives and related organic compounds with modulated specificities have been developed and several are in clinical trials as anticancer drugs. They all share an indolo[2,3-]carbazole aglycon which binds to the ATP binding site and can hydrogen bond with two conserved amino acids. For this class of inhibitors, specificity for a particular protein kinase can be achieved by the moiety which is attached to the indole nitrogen atoms.

Exemplary compounds and compositions in the patent database, which are claimed as protein kinase inhibitors, include the following:

U.S. Pat. No. 6,613,776, issued Sep. 2, 2003 to Knegtel, et al. discloses pyrazole compositions useful as protein kinase inhibitors, especially as inhibitors of aurora-2 and GSK-3, for treating diseases such as cancer, diabetes, and Alzheimer's disease.

U.S. Pat. No. 6,593,357, issued Jul. 15, 2003 to Green, et al. discloses pyrazole compositions useful as protein kinase inhibitors of ERK, for treating disease states in mammals that are alleviated by a protein kinase inhibitor, particularly diseases such as cancer, inflammatory disorders, restenosis, and cardiovascular disease.

U.S. Pat. No. 6,555,539, issued Apr. 29, 2003 to Reich, et al. discloses indazole compounds that modulate and/or inhibit cell proliferation, such as the activity of protein kinases, for mediating kinase-dependent diseases and treating cancer and other disease states associated with unwanted angiogenesis and/or cellular proliferation, such as diabetic retinopathy, neovascular glaucoma, rheumatoid arthritis, and psoriasis.

U.S. Pat. No. 6,451,838, issued Sep. 17, 2002 to Moon, et al. discloses 1-pyrrolidin-1-ylmethyl-3-(pyrrol-2-ylmethylidene)-2-indolinone derivatives for modulating the activity of protein kinases, methods of preparing same, along with pharmaceutical compositions comprising these compounds and methods of treating diseases related to abnormal protein kinase activity utilizing pharmaceutical compositions comprising these compounds.

U.S. Pub. No. 2005/0171076 (U.S. patent application Ser. No. 11/045,331, filed Jan. 31, 2005) to Eric Meggers, et al., the contents of which are incorporated herein by reference in their entirety, describes metal complex protein kinase inhibitors that target the ATP binding site of protein kinases.

There remains is a significant need in the art for more specific and effective protein kinase inhibitors, which can be targeted to specific tissues and/or disease states.

SUMMARY OF THE INVENTION

Provided are novel organometallic compounds that inhibit protein kinases, including PI3K lipid kinase and phospho-AKT in human melanoma cells, and also inhibit the migration and proliferation of melanoma cells.

Disclosed are compounds according to formula I:

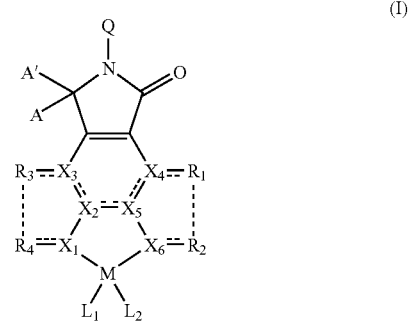

(I)

or a pharmaceutically acceptable salt or ester thereof, wherein:

$X_1$, $X_2$, $X_3$, $X_4$, $X_5$, and $X_6$ are each independently N, C, S, O, B, or Si;

$R_1$ and $R_2$ are taken together to form a mono-, bi- or tricyclic, carbo- or heterocyclic ring, wherein the ring is either unsubstituted or substituted in one or more position(s) with halo, hydroxyl, carbonyl, nitro, amino, trihaloalkyl, substituted or unsubstituted $C_1$-$C_4$ alkoxy, substituted or unsubstituted straight or branched $C_1$-$C_6$ alkyl-OH, substituted or unsubstituted straight or branched $C_1$-$C_6$ alkyl-$NH_2$, $C_1$-$C_4$ alkenyloxy, aryl, aralkyl, phenoxy, benzyloxy, or any other hydrogen bond donor or acceptor, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S, and/or $R_3$ and $R_4$ are taken together to form a mono-, bi- or tricyclic, carbo-, or heterocyclic ring, wherein the ring is either unsubstituted or substituted in one or more position(s) with halo, hydroxyl, carbonyl, nitro, amino, trihaloalkyl, substituted or unsubstituted $C_1$-$C_4$ alkoxy, substituted or unsubstituted straight or branched $C_1$-$C_6$ alkyl-OH, substituted or unsubstituted straight or branched $C_1$-$C_6$ alkyl-$NH_2$, $C_1$-$C_4$ alkenyloxy, aryl, aralkyl, phenoxy, benzyloxy, or any other hydrogen bond donor or acceptor, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S;

M is Ru, Pt, Tc, Re, Os, Rh, Ir, Pd, Au, Cu, Fe, Co, or Cr;

Q is straight or branched chain $C_1$-$C_6$ alkyl or alkenyl, optionally substituted with halo, hydroxyl, nitro, trifluoromethyl, $C_1$-$C_4$ straight or branched chain alkyl or alkenyl, $C_1$-$C_4$ alkoxy, $C_1$-$C_4$ alkenyloxy, phenoxy, benzyloxy, or amino;

A and A' are each independently hydrogen, hydroxy, hydroxymethyl, $C_1$-$C_6$ straight or branched chain alkyl, $C_2$-$C_6$ straight or branched chain alkenyl, O—($C_1$-$C_6$ straight or branched chain alkyl), or O—($C_2$-$C_6$ straight or branched chain alkenyl), or A and A' are taken together as =O; and each $L_1$ and $L_2$ are independently a monodentate ligand capable of acting as a ligand for said metal M, a bidentate ligand capable of acting as a ligand for said metal M, or a tridentate ligand capable of acting as a ligand for said metal M;

wherein at least one of $R^1$ and $R^2$ taken together and $R^3$ and $R^4$ taken together form a mono-, bi-, or tricyclic carbo- or heterocyclic ring.

Also disclosed are pharmaceutical compositions comprising a formula of compound I according to the preceding definition.

The present invention is also directed to methods for inhibiting cancer cell proliferation, migration or both comprising contacting a cancer cell with a compound of formula I. Also disclosed are methods for treating a kinase-affected disease or condition comprising administering to a subject in need thereof a therapeutically effective amount of a compound of formula I.

DETAILED DESCRIPTION OF ILLUSTRATIVE EMBODIMENTS

Figure 1D:
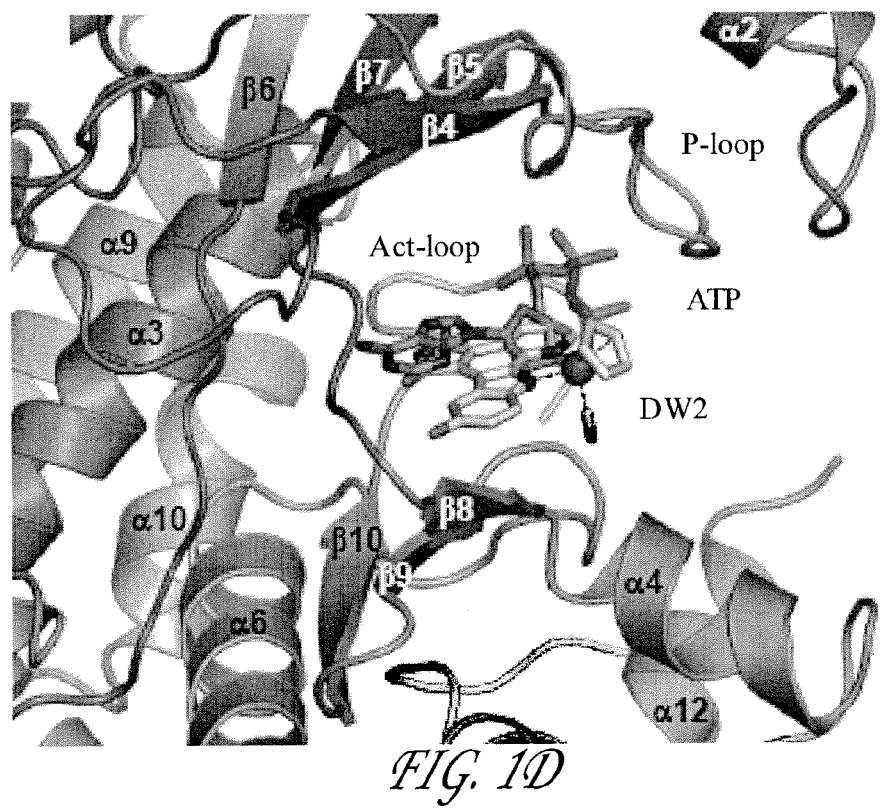
FIG. 1 depicts the process of initial lead inhibitor identification and crystal structure of PI3Kγ in complex with DW2.

Provided are metal complexes that target the ATP binding site of protein kinases, and methods involving the use of such metal complex kinase inhibitors. Additional ligands in the coordination sphere of the metal ion undergo additional specific contacts with other parts of the active site, yielding metal complex binders with high affinity and specificity for particular protein kinases.

The present invention may be understood more readily by reference to the following detailed description taken in connection with the accompanying figures and examples, which form a part of this disclosure. It is to be understood that this invention is not limited to the specific products, methods, conditions, or parameters described and/or shown herein, and that the terminology used herein is for the purpose of describing particular embodiments by way of example only and is not intended to be limiting of the claimed invention.

In the present disclosure the singular forms "a," "an," and "the" include the plural reference, and reference to a particular numerical value includes at least that particular value, unless the context clearly indicates otherwise. Thus, for example, a reference to "a substituent" or "the substituent" is a reference to one or more of such substituents and equivalents thereof known to those skilled in the art, and so forth. When values are expressed as approximations, by use of the antecedent "about," it will be understood that the particular value forms another embodiment.

The disclosures of each patent, patent application, and publication cited or described in this document are hereby incorporated herein by reference, in their entirety.

As employed above and throughout the disclosure unless otherwise specified, the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects. As an example, the compounds useful in the methods of the present invention are administered at a dosage and for a time such that the level of activation and adhesion activity of platelets is reduced as compared to the level of activity before the start of treatment. The term "therapeutically effective amount" as used herein can refer to that amount of a compound which will contribute to the cancer-treating ability of the composition.

The term "treating" as used herein refers to partial or total inhibition of a disease state, disease progression, or disorder. The terms "treatment" or "therapy" (as well as different word forms thereof) includes preventative (e.g., prophylactic), curative or palliative treatment. The term "preventing" as used herein refers to either preventing the onset of clinically evident disease or disorder altogether or with regard to one or more phenotypes or symptoms thereof, or preventing the onset of a preclinically evident stage of a disease or disorder in individuals at risk. The term "enhancing" the biological activity, function, health, or condition of an organism refers to the process of augmenting, fortifying, strengthening, or improving.

The term "isomers" refer to different compounds that have the same molecular formula. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

As used herein, unless otherwise specified, "alkenyl" refers to an alkyl radical having from about 2 to about 20 carbon atoms and one or more double bonds (and all combinations and subcombinations of ranges and specific numbers of carbon atoms therein), wherein alkyl is as previously defined. In some embodiments, it is preferred that the alkenyl groups have from about 2 to about 6 carbon atoms. Alkenyl groups may be optionally substituted.

Typically, substituted chemical moieties include one or more substituents that replace hydrogen. Exemplary substituents include, for example, halo (e.g., F, Cl, Br, I), alkyl, cycloalkyl, alkylcycloalkyl, cycloalkylalkyl, alkenyl, alkynyl, aralkyl, aryl, heteroaryl, heteroaralkyl, spiroalkyl, heterocycloalkyl, hydroxyl (—OH), nitro (—NO$_2$), cyano (—CN), amino (—NH$_2$), —N-substituted amino (—NHR"), —N,N-disubstituted amino (—N(R")R"), oxo (=O), carboxy (—COOH), —O—C(=O)R", —C(=O)R", —OR", —C(=O)OR", -(alkylene)-C(=O)—OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (—SR"), sulfonic acid (—SO$_3$H), phosphonic acid (—PO$_3$H), —P(=O)(OR")OR", —S(=O)R", —S(=O)$_2$R", —S(=O)$_2$ NH$_2$, —S(=O)$_2$NHR", —S(=O)$_2$NR"R", —NHS(=O)$_2$R", —NR"S(=O)$_2$R", —CF$_3$, —CF$_2$CF$_3$, —NHC(=O)NHR", —NHC(=O)NR"R", —NR"C(=O)NHR", —NR"C(=O)NR"R", —NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example. Those skilled in the art can readily identify other appropriate substituents.

The term "pharmaceutically acceptable salt, ester, or solvate" refers to a salt, ester, or solvate of a subject compound which possesses the desired pharmacological activity and which is neither biologically nor otherwise undesirable. A salt, ester, or solvate can be formed with inorganic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride, hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Examples of base salts, esters, or solvates include ammonium salts; alkali metal salts, such as sodium and potassium salts; alkaline earth metal salts, such as calcium and magnesium salts; salts with organic bases, such as dicyclohexylamine salts; N-methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; aralkyl halides, such as benzyl and phenethyl bromides; and others. Water or oil-soluble or dispersible products are thereby obtained.

The term "ligand" as used herein refers to any group which can form a coordination complex with a metal. A ligand offering one group for attachment to the metal is termed monodentate; two groups, bidentate; three or more groups, polydentate. A ligand may attach to the metal atom by covalent or ionic bond(s). Many compounds, too numerous to fully enumerate here, can act as ligands; common ligands include, but are not limited to, derivatives of amines (e.g. ethylenediamine), aldehydes and ketones, carboxylic acids (e.g., ethylenediaminetetraacetic acid (EDTA)), sulfonyl- and mercapto-derivative groups, phosphoryls and other phorphorus derivatives, hydroxamic acid derivatives, and various combinations thereof. Other examples of useful metal ligands include, without limitation, mercapto derivatives, hydroxamic acid derivatives, phosphorus derivatives (particularly those of the general formula X—P(O)(OH)—R, wherein R is as defined above for R1), carboxyl derivatives, N-carboxyalkyl derivatives, aldehydes, ketones, and combinations thereof. In particular, useful ligands include, without limitation, derivatives of dicarboxylic acids, -diketones, -hydroxycarboxylic acids, alkyl and aryl diamines, and -aminocarboxylates (including amino acid derivatives), thioethers, xanthates, dithiocarbamates, dithiocarboxylates, thioglycolates, thiols, and diphosphines.

The term "monodentate ligand" as used herein refers to an atom or compound which has one lone pair of electrons by which it can attach to another atom or compound. For example, many simple anions, or Lewis bases, can act as monodentate ligands, including, without limitation, chloride ion, hydroxide ion, water, and ammonia. In addition, a monodentate ligand can also be a compound which coordinates through a pi-bond, such as an alkene.

The term "bidentate ligand" as used herein refers to an atom or compound which has two lone pairs of electrons by which it can attach to another atom or compound. Similarly, the terms "tridentate ligand" and "tetradentate ligand" as used herein refer to an atom or compound which has, respectively, three and four lone pairs of electrons by which it can attach to another atom or compound.

The development of small molecules that perturb specific protein functions is of great importance for probing biological processes and ultimately for the development of potent and safe drugs. Medicinal chemistry is predominately focused on the design of organic molecules, whereas the incorporation of inorganic components into drugs is much less investigated. Furthermore, in almost all metallopharmaceuticals, the metal ion possesses a reactive feature. We have found that certain organometallic and inorganic compounds are useful as structural scaffolds for enzyme inhibition. Such metal-ligand assemblies allow convergent synthetic approaches and give access to structural motifs that differ from purely organic molecules.

Protein kinases regulate most aspects of cellular life and are one of the main drug targets. The microbial alkaloid staurosporine is a very potent, but relatively nonspecific inhibitor of many protein kinases. Many staurosporine derivatives and related organic compounds with modulated specificities have been developed and several are in clinical trials as anticancer drugs. They all share an indolo[2,3-]carbazole aglycon (1) which binds to the ATP binding site and can hydrogen bond with two conserved amino acids. For this class of inhibitors, specificity for a particular protein kinase can be achieved by the moiety which is attached to the indole nitrogen atoms.

As depicted in FIG. 1, it had previously been determined that by replacing the indolocarbazole alkaloid scaffold with metal complex (2), elaborate structures could be assembled in an efficient manner by variation of ligand(s) (LX) (see U.S. Pub. No. 2005/0171076 (U.S. patent application Ser. No. 11/045,331, filed Jan. 31, 2005)). Components of the design include ligands (3) and (4), derived from the indolocarbazole aglycon (1) by just replacing two carbon against two nitrogen atoms. This transformation does not change the shape of the ligand but generates two benzimidazole moieties that can function as coordination sites for the metal center. The remaining coordination sites at the metal center can become filled-up by ligands L1 to L4 and substitute for the carbohydrate moiety, with the metal center serving as a "glue" for holding all parts together.

Medicinal Chemistry of Small Organic Compounds. New technologies for drug discovery such as combinatorial chemistry, high-throughput screening, computer assisted drug design, and virtual compound screening in silico emerged during the last 20 years. Interestingly, despite these clearly extremely powerful techniques, the development of high affinity and specific compounds for a given target is still a great and often unsolved challenge. For example, not a single existing kinase inhibitor is specific for a particular kinase. It is also surprising that despite all technical advances the number of new drug launches by the top 20 pharmaceutical companies is not increasing despite an increase in spending into research and development.

One limiting factor can be found in the synthesis itself of the drug candidates. For example, complex natural products often show promising biological activities and would be interesting lead structures, but they often require too many reaction steps including time consuming purifications and are therefore often not practical as drug scaffolds. For example, bryostatin, a member of marine derived macrolactones, is extremely potent against numerous cancers but its synthesis includes more than 60 reaction steps. The Wender group has addressed this issue by developing analogs with improved synthetic accessibility, but the synthesis is still around 20 steps long. There is clearly a need for simplification of synthetic approaches. Additionally, the desire to make large compound libraries has led to the use of reliable chemistry and simple scaffolds. It is therefore no surprise that the diversity of topological shapes of known drugs is extremely low. A report about the analysis of the Comprehensive Medicinal Chemistry (CMC) database revealed that half of the known drugs fall into only 32 shape categories (out of more than 5000 compounds analyzed). Most of the 32 frameworks contain at least two six-membered rings linked or fused together.

It can be concluded that the popularity of molecular scaffolds for drugs is dictated by synthetic availability and the adaptability to combinatorial chemistry.

Metallopharmaceuticals. Metal ions and metal complexes are important in diagnosis and therapy and metal ions from all over the periodic table of elements are being used. In all metallopharmaceuticals, the metal-ion bears the key feature of the mechanism. For example, the highly efficient anticancer drug cisplatin reacts with DNA by crosslinking guanine bases which eventually leads to apoptosis.

One of the rare reported metal complexes in which the metal plays only a structural role is the copper complex diaqua[bis(2-pyridylcarbonyl)amido]copper(II) nitrate dihydrate. This complex was found to fit in the enzyme active site by modeling and experimentally characterized to be a competitive inhibitor of HIV-1 protease. To the best of the authors knowledge, not a single FDA approved metallopharmaceutical exists in which the metal plays a purely structural role in organizing the attached organic ligands.

Metal Complexes as Structural Templates. Metal coordination has been proven to be a powerful tool for the creation of artificial receptors, for the self-assembly of elaborated nanostructures, for the assembly of biomimetic structures such as DNA mimicking helicates, for the synthesis of dendrimers, and the generation of liquid crystals. In addition to playing an important role in the assembly process, the metal complex often fulfills an important structural role in organizing the surrounding organic part. Ligand exchange kinetics can be tuned by the nature of the metal and its oxidation state and a change in coordination number and geometry allows a modification of organization of the attached organic ligands. Thus, metal complexes should clearly be very interesting structural templates for the creating of enzyme inhibitors. The metal center will allow efficient assembly reactions and will give the opportunity to generate structural motifs that are not easily accessible with purely organic compounds.

Metal Toxicity. A significant concern in using metal containing drugs is the potential toxicity of the metal. Clearly many essential and non-essential metals or metal compounds of Be, Cr, Cd, Ni, Co, Pb, and Hg are toxic and/or carcinogenic. However, it is important to recognize that the action of these metals is closely associated to their oxidation state and involvement of all additional metal ligands. For example, chromium is cancerogenic in the form of $CrO_4^{2-}$, but not in the oxidation state +2 and +3, because only the chromate ion can enter the cells through a specific anion transporter. In another example, cisplatin, $PtCl_2(NH_3)_2$, is one of the most successful anticancer drugs and also very toxic. The toxicity is related to the reactivity of the metal center due to exchange of the chlorides and therefore its potency and toxicity are highly dependent on the substituents. A reduction in reactivity correlates with a reduction of toxicity. From this it can be concluded that toxicity and function of metals are closely connected to the nature of the ligands. A metal complex that has an inert coordination sphere might not display any "metal-specific" toxicity itself.

In a metal-containing compound, the ligand is often an organic compound that binds the metal ion and modifies the physical and chemical properties of the ion. Thus, kinetic stability of the metal-ligand assembly will be an important factor for toxicity. Almost nothing is known about short and long term toxicity and pharmacokinetics of kinetically inert metal complexes and the risk of metal accumulation.

Stability of Metal Complexes. The rate of ligand substitutions is an important parameter for the stability of metal complexes in biological environment. It depends on the nature of the ligand and importantly on the metal itself and its oxidation state. Metals of the first d-series such as Mn2+, Fe2+/3+, Co2+, Ni2+, Cu2+, and Zn2+ generally undergo rapid equilibration. Exceptions in the first row are classical coordination complexes of Cr3+ and Co3+ because of their ability to from strong-field d3 and d6 complexes, respectively, and some organometallic scaffolds such as ferrocene and chromium plus iron carbonyl compounds. Among the second and third d-series complexes the inertness is generally much higher, which reflects the high ligand field stabilization energy and the strength of the metal-ligand bonds. For example, Ru—N and Pt—N bonds can be considered as completely inert against substitution at ambient temperature and can thus de facto be treated like covalent bonds. Additionally, the ability to tune the kinetic stability of coordinative bonds without changing the overall structure, can be a useful advantages in the drug discovery process.

Our initial compounds showed a limited stability of the ruthenium complexes (only one complex was completely stable), probably due to the unfavorable biting angle of the bisbenzimidazole ligand. We have also synthesized a more stable second-generation ligand S5, which solves the stability problem and even yields more potent inhibitors.

Metal Complexes as Protein Kinase Inhibitors. Protein kinases regulate most aspects of cellular function in eukaryotes, including metabolism, transcription, cell cycle progression, apoptosis, differentiation, and intercellular communication. Mutations and dysregulation of protein kinases play causal roles in many human diseases, making kinases an important therapeutic target. Protein kinases are among the largest enzyme families with more than 500 putative protein kinase genes, which makes it challenging to find specific inhibitors. An in vitro study of the specificity of 28 commercially available protein kinase inhibitors, some with supposedly high specificity, revealed that all but two drugs had more than one protein target. Clearly, novel and if possible general strategies have to be sought in order to solve the important problem of developing specific inhibitors for enzymes that are members of large and homologous enzyme families.

Typically, protein kinase inhibitors bind to the ATP binding site by mimicking the hydrogen-bonding pattern of the adenine base. Given the high degree of amino acid conversation within the ATP binding pocket of protein kinases, the design of highly selective ATP-competitive inhibitors was long believed to be impossible. This notion has be changed and successful examples have demonstrated that it is possible to take advantage of the small differences between the structures of the APT binding sites, even between closely related protein kinases. Inhibitors are generally made up of a heterocyclic core that roughly mimics adenine. Like adenine, these templates form hydrogen bonds with the extended coil stretch of the kinase. Affinity and selectivity for a particular kinase are achieved by modifying one of the main templates resulting in modulated interactions with the ATP binding site.

Provided are compounds according to formula I:

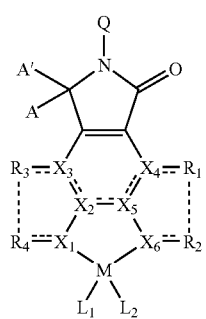

(I)

or a pharmaceutically acceptable salt or ester thereof, wherein:

$X_1, X_2, X_3, X_4, X_5$, and $X_6$ are each independently N, C, S, O, B, or Si;

$R_1$ and $R_2$ are taken together to form a mono-, bi- or tricyclic, carbo- or heterocyclic ring, wherein the ring is either unsubstituted or substituted in one or more position(s) with halo, hydroxyl, carbonyl, nitro, amino, trihaloalkyl, substituted or unsubstituted $C_1$-$C_4$ alkoxy, substituted or unsubstituted straight or branched $C_1$-$C_6$ alkyl-OH, substituted or unsubstituted straight or branched $C_1$-$C_6$ alkyl-NH$_2$, $C_1$-$C_4$ alkenyloxy, aryl, aralkyl, phenoxy, benzyloxy, or any other hydrogen bond donor or acceptor, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S, and/or $R_3$ and $R_4$ are taken together to form a mono-, bi- or tricyclic, carbo-, or heterocyclic ring, wherein the ring is either unsubstituted or substituted in one or more position(s) with halo, hydroxyl, carbonyl, nitro, amino, trihaloalkyl, substituted or unsubstituted $C_1$-$C_4$ alkoxy, substituted or unsubstituted straight or branched $C_1$-$C_6$ alkyl-OH, substituted or unsubstituted straight or branched $C_1$-$C_6$ alkyl-NH$_2$, $C_1$-$C_4$ alkenyloxy, aryl, aralkyl, phenoxy, benzyloxy, or any other hydrogen bond donor or acceptor, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S;

M is Ru, Pt, Tc, Re, Os, Rh, Ir, Pd, Au, Cu, Fe, Co, or Cr;

Q is straight or branched chain $C_1$-$C_6$ alkyl or alkenyl, optionally substituted with halo, hydroxyl, nitro, trifluoromethyl, $C_1$-$C_4$ straight or branched chain alkyl or alkenyl, $C_1$-$C_4$ alkoxy, $C_1$-$C_4$ alkenyloxy, phenoxy, benzyloxy, or amino;

A and A' are each independently hydrogen, hydroxy, hydroxymethyl, $C_1$-$C_6$ straight or branched chain alkyl, $C_2$-$C_6$ straight or branched chain alkenyl, O—($C_1$-$C_6$ straight or branched chain alkyl), or O—($C_2$-$C_6$ straight or branched chain alkenyl), or A and A' are taken together as =O; and each $L_1$ and $L_2$ are independently a monodentate ligand capable of acting as a ligand for said metal M, a bidentate ligand capable of acting as a ligand for said metal M, or a tridentate ligand capable of acting as a ligand for said metal M;

wherein at least one of $R^1$ and $R^2$ taken together and $R^3$ and $R^4$ taken together form a mono-, bi-, or tricyclic carbo- or heterocyclic ring.

$L_1$ and $L_2$ may independently comprise halo, hydroxy, carbonyl, amine, nitro, sulfhydryl, pyridine, thiolate, histidine, methionine, cysteine, dimethylsulfoxide, substituted or unsubstituted pyridines, substituted or unsubstituted amines, substituted or unsubstituted diamines, substituted or unsubstituted thiols, substituted or unsubstituted dithiols, substituted or unsubstituted imidazoles, substituted or unsubstituted pyrazoles, substituted or unsubstituted benzimidazoles, substituted or unsubstituted 1,4-dienes, substituted or unsubstituted 2-(aminomethyl)pyridines, substituted or unsubstituted 2-iminopyridines, substituted bipyridines, substituted or unsubstituted phenanthrolines, substituted or unsubstituted 8-hydroxyquinolines, substituted or unsubstituted 6-mercaptopurines, or substituted or unsubstituted phosphines.

In preferred embodiments, $X_1, X_2, X_3, X_4, X_5$, and $X_6$ may independently comprise N or C.

M may be Ru or Pt in certain preferred embodiments.

$R_1$ and $R_2$ may be taken together to form a monocyclic 5 or 6 membered ring, or a bicyclic indene, indene dericative, naphthalene, or naphthalene derivative ring, and wherein the ring is carbocyclic or heterocyclic. $R_3$ and $R_4$ may be taken together to form a monocyclic 5 or 6 membered ring, or a bicyclic indene, indene derivative, naphthalene, or naphthalene derivative ring, and wherein the ring is carbocyclic or heterocyclic.

The instant compounds may comprise a compound of formula II

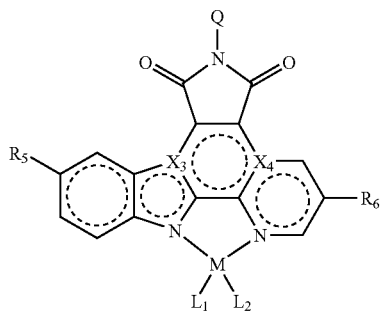

(II)

or a pharmaceutically acceptable salt or ester thereof, wherein:

$X_3$ and $X_4$ are each independently N or C;

$R_5$ is halo, hydroxyl, carbonyl, nitro, amino, $C_1$-$C_4$ alkoxy, $C_1$-$C_4$ alkyl-OH, $C_1$-$C_4$ alkyl-OH, $NH_2$, $C_1$-$C_4$ alkenyloxy, aryl, aralkyl, phenoxy, or benzyloxy;

$R_6$ is fluoro, hydroxyl, amino, trifluoroalkyl, chloroform, substituted or unsubstituted $C_1$-$C_6$ straight or branched alkyl-OH, substituted or unsubstituted $C_1$-$C_6$ straight or branched alkyl-$NH_2$, or any other hydrogen bond donor or acceptor; and, M is Ru or Pt.

The present compounds may comprise a compound of formula III

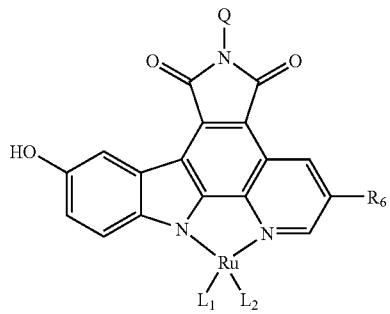

(III)

or a pharmaceutically acceptable salt or ester thereof, wherein:

$L_1$ and $L_2$ are independently a monodentate ligand capable of acting as a ligand for said metal M.

In a compound of formula III, $L_1$ may be —C≡O$^+$, and $L_2$ may be an optionally substituted aromatic carbocyclic ring. $L_2$ may be an optionally substituted pentane ring, and the pentane ring may be monosubstituted or polysubstituted.

Also in a compound of formula III, $R_6$ may fluorine, and independently, Q may be methyl.

The present compounds may comprise a compound of formula IV

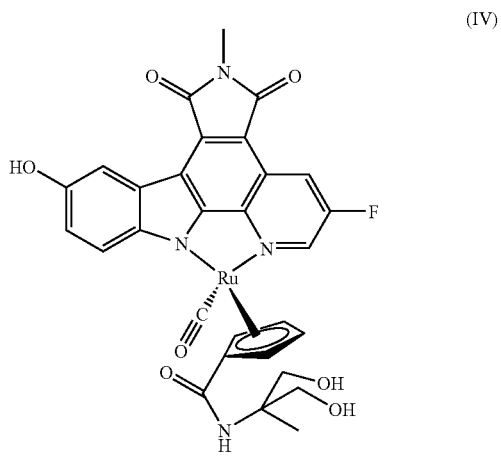

(IV)

Also provided are pharmaceutical compositions comprising a compound according to any of the conditions described above with respect to the inventive compounds. The present invention is also directed to methods for inhibiting cancer cell proliferation, migration, or both, comprising contacting a cancer cell with a compound according to any of the conditions described above with respect to the inventive compounds. Also disclosed are methods for treating a kinase-affected disease or condition comprising administering to a subject in need thereof a therapeutically effective amount of a compound of formula I.

The novel pharmaceutical compositions of the inventive subject matter include, and the instant methods employ, a therapeutically effective amount of the active agent indicated above. This effective amount will generally comprise from about 0.1 mg to about 100 mg of the active agent per kilogram of patient body weight per day. This effective amount can vary depending upon the physical status of the patient and other factors well known in the art. Moreover, it will be understood that this dosage of active agent can be administered in a single or multiple dosage units to provide the desired therapeutic effect. If desired, other therapeutic agents can be employed in conjunction with those provided by the present inventive subject matter.

The compounds of the inventive subject matter are preferably delivered to the patient by means of a pharmaceutically acceptable carrier. Such carriers are well known in the art and generally will be in either solid or liquid form. Solid form pharmaceutical preparations which may be prepared according to the present inventive subject matter include powders, tablets, dispersible granules, capsules, cachets and suppositories. In general, solid form preparations will comprise from about 5% to about 90% by weight of the active agent.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating materials as a carrier which may provide a capsule in which the active component (with or without other carriers) is surrounded by carrier, which is thus in association with it. Similarly, cachets are included. Tablets, powders, cachets, and capsules can be used as solid dosage forms suitable for oral administration. If desired for reasons of convenience or patient acceptance, pharmaceutical tablets prepared according to the inventive subject matter may be provided in chewable form, using techniques well known in the art.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water/propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizers and thickening agents as desired. Aqueous suspensions suitable for oral use can be made my dispersing the finely divided active component in water with a viscous material, i.e., natural or synthetic gums, resins, methylcellulose, sodium carboxymethylcellulose, and other well known suspending agents. Liquid pharmaceutical preparations may comprise up to 100% by weight of the subject active agent.

Also contemplated as suitable carriers are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. Naturally, the liquid utilized will be chosen with regard to the route of administration. For example, liquid preparations containing large amounts of ethanol are not suitable for parenteral use.

The pharmaceutical preparation may also be in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The pharmaceutical preparations of the inventive subject matter may include one or more preservatives well known in the art, such as benzoic acid, sorbic acid, methylparaben, propylparaben and ethylenediaminetetraacetic acid (EDTA). Preservatives are generally present in amounts up to about 1% and preferably from about 0.05 to about 0.5% by weight of the pharmaceutical composition.

Useful buffers for purposes of the inventive subject matter include citric acid-sodium citrate, phosphoric acid-sodium phosphate, and acetic acid-sodium acetate in amounts up to about 1% and preferably from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the pharmaceutical composition.

Sweeteners which may be employed include those sweeteners, both natural and artificial, well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition.

Flavorants which may be employed in the pharmaceutical products of the inventive subject matter include both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the pharmaceutical composition.

Colorants useful in the present inventive subject matter include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D.&C. dyes and the like. Such dyes are generally present in amounts up to about 0.25% and preferably from about 0.05% to about 0.2% by weight of the pharmaceutical composition. A full recitation of all F.D.&C. and D.&C. dyes and their corresponding chemical structures may be found in the Kirk-Othmer Encyclopedia of Chemical Technology, in Volume 5, at pages 857-884, which text is accordingly incorporated herein by reference.

Useful solubilizers include alcohol, propylene glycol, polyethylene glycol and the like and may be used to solubilize the flavors. Solubilizing agents are generally present in amounts up to about 10%; preferably from about 2% to about 5% by weight of the pharmaceutical composition.

Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

It is not expected that compounds of the present inventive subject matter will display significant adverse interactions with other synthetic or naturally occurring substances. Thus, a compound of the present inventive subject matter may be administered in combination with other compounds and compositions useful for . . . . In particular the compounds of the present inventive subject matter may be administered in combination with other compounds of the present inventive subject matter; other anticancer substances; etc.

The optimal pharmaceutical formulations will be determined by one skilled in the art depending upon considerations such as the route of administration and desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the present therapeutic agents of the inventive subject matter.

Route(s) of Administration

The route(s) of administration of the compounds and compositions of the present inventive subject matter are well known to those skilled in the art (see, for example, "Remington's Pharmaceutical Sciences", 18th Edition, Chapter 86, pp. 1581-1592, Mack Publishing Company, 1990). The compounds and compositions may be administered orally, parenterally, by inhalation spray, topically, rectally, nasally, buccally, vaginally, or via an implanted reservoir in dosage formulations containing conventional non-toxic pharmaceutically-acceptable carriers, adjuvants, and vehicles. The term parenteral as used herein includes subcutaneous, intravenous, intramuscular, intraperitoneally, intrathecally, intraventricularly, intrasternal, and intracranial injection or infusion techniques.

To be effective therapeutically as central nervous system targets, the compounds and compositions should readily penetrate the blood-brain barrier when peripherally administered. Compounds which cannot penetrate the blood-brain barrier can be effectively administered by an intraventricular route.

The compounds and compositions may be administered in the form of sterile injectable preparations, for example, as sterile injectable aqueous or oleaginous suspensions. These suspensions, may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

Additionally, in a preferred embodiment, the compounds and compositions may be administered orally in the form of capsules, tablets, aqueous suspensions, or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening, flavoring, coloring agents, or combinations thereof. Delivery in an enterically coated tablet, caplet, or capsule, to further enhance stability and provide release in the intestinal tract to improve absorption, is the best mode of administration currently contemplated.

The compounds may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax, and polyethylene glycols.

Furthermore, the compounds may be administered topically, especially when the conditions addressed for treatment involve areas or organs readily accessible by topical application, including the lower intestinal tract. Suitable topical formulations can be readily prepared for such areas or organs. For example, topical application to the lower intestinal tract can be effected in a rectal suppository formulations (see above) or in suitable enema formulations.

It is envisioned that the continuous administration or sustained delivery of the compounds and compositions of the present inventive subject matter may be advantageous for a given condition. While continuous administration may be accomplished via a mechanical means, such as with an infusion pump, it is contemplated that other modes of continuous or near continuous administration may be practiced. For example, such administration may be by subcutaneous or muscular injections as well as oral pills.

Techniques for formulating a variety of other sustained- or controlled-delivery means, such as liposome carriers, bio-erodible particles or beads and depot injections, are also known to those skilled in the art.

Dosage.

Dosage levels on the order of about 0.001 mg to about 100 mg per kilogram body weight of the active ingredient compounds or compositions are useful in the treatment of the above conditions, with preferred levels ranging from 200 mg per day to 1600 mg per day. The compounds and compositions of the present inventive subject matter may usually be given in two or three doses daily. Starting with a low dose (200-300 mg) twice daily and slowly working up to higher doses if needed is a preferred strategy. The amount of active ingredient that may be combined with the carrier materials to produce a single dosage form will vary depending upon the host treated and the particular mode of administration.

It is understood, however, that a specific dose level for any particular patient will depend upon a variety of factors, including the activity of the specific compound employed; the age, body weight, general health, sex and diet of the patient; the time of administration; the rate of excretion; drug combination; the severity of the particular disorder being treated; and the form of administration. One of ordinary skill in the art would appreciate the variability of such factors and would be able to establish specific dose levels using no more than routine experimentation.

EXAMPLES

The following examples are illustrative of the present inventive subject matter and are not intended to be limitations thereon. Unless otherwise indicated, all percentages are based upon 100% by weight of the final composition.

Example 1

Synthesis of Inventive Compounds

The compounds of the present inventive subject matter may be readily prepared by standard techniques of organic chemistry, utilizing the general synthetic pathways depicted below.

In the preparation of the compounds of the inventive subject matter, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, ed., Plenum Press, New York, N.Y.; and "Protective Groups in Organic Synthesis," Greene, ed., John Wiley & Sons, New York, N.Y. (1981) for the teaching of protective groups which may be useful in the preparation of compounds of the present inventive subject matter.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g., reverse phase HPLC), column chromatography, flash chromatography, radial chromatography, trituration, and the like.

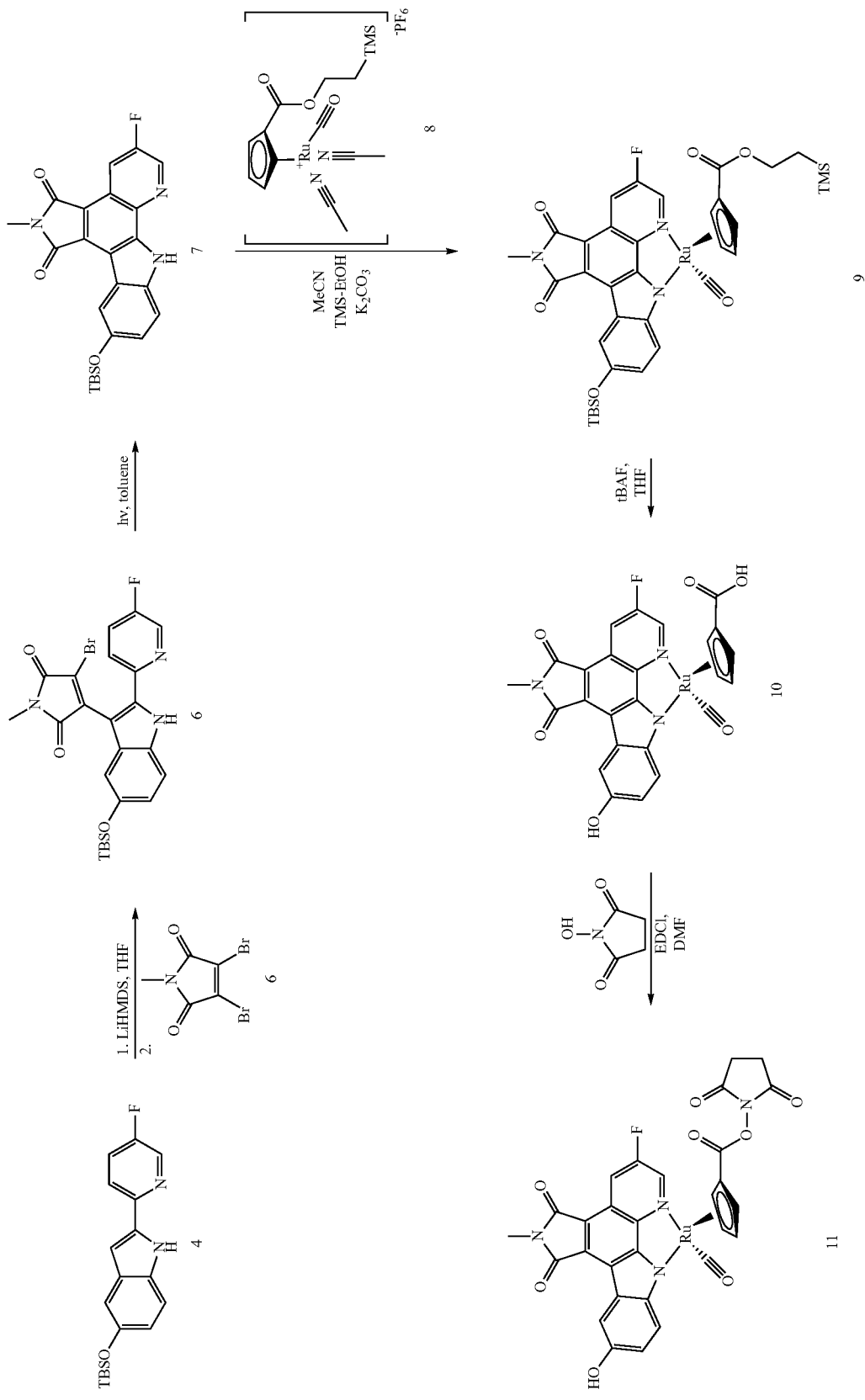
Scheme 1-Synthesis of library precursor 11.

LiHMDS=lithium hexamethyl disilylazide, MeCN=acetonitrile, tBAF=tetrabutylammonium fluoride, EDCI=1-ethyl-3-(3'-dimethylaminopropyl)carbodiimide, DMF=dimethylformamide.

9.82 (s, 1H), 8.98 (dd, J=9.3, 2.8 Hz, 1H), 8.87 (dd, J=2.8, 0.5 Hz, 1H), 8.55 (dd, J=1.9, 0.6 Hz, 1H), 7.52 (dd, J=8.7, 0.5 Hz, 1H), 7.17 (dd, J=8.7, 2.5 Hz, 1H), 3.30 (s, 1H), 1.08 (s, 9H), 0.35 (s, 6H). IR (thin film) ν (cm$^{-1}$)=3317, 2929, 2856, 1694,

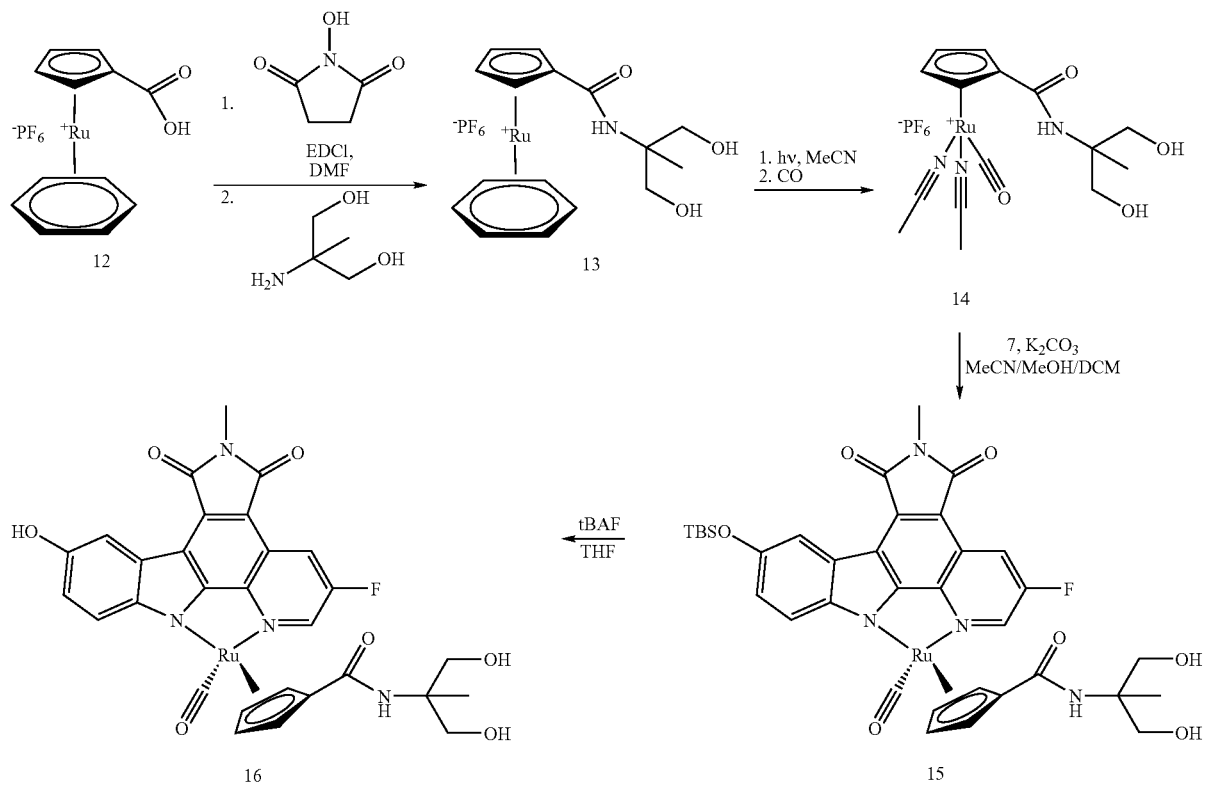

Compound 6: Compound 4 (Pagano, N., Maksimoska, J., Bregman, H., Williams, D. S., Webster, R. D., Xue, F., and Meggers, E. (2007) *Ruthenium half-sandwich complexes as protein kinase inhibitors: derivatization of the pyridocarbazole pharmacophore ligand, Org Biomol Chem* 5, 1218-1227) (508 mg, 1.48 mmol) was dissolved in THF (6 ml). The resulting solution was purged with argon and cooled to −20° C. A solution of lithium hexamethyl disilylazide (2.97 ml of a 1 M solution in THF, 2.97 mmol) was added drop-wise to this solution. The reaction was then stirred for 45 minutes at −20° C. A cold (−20° C.) solution of 5 (400 mg in 6 ml of THF) was then added all at once. The resulting solution was stirred for 16 hours while warming to room temperature. The reaction was then quenched with 1 M HCl (25 ml) and extracted into EtOAc (3×). The combined organic layers were washed with saturated aqueous NaHCO$_3$, H$_2$O, and brine, dried over Na$_2$SO$_4$, and evaporated resulting in a brown oil. This material was then carried on crude.

Compound 7: Crude compound 6 was dissolved in toluene (250 ml), purged with argon, and irradiated with a medium pressure mercury lamp (450 W) through a uranium filter for three hours. The resulting orange/brown solution was evaporated, redissolved in minimal DCM/MeOH and adsorbed onto silica gel. The material was purified via silica gel chromatography eluting with Hex:EtOAc 8:1 ramping to 5:1. The desired product 7 was isolated as an orange solid (160 mg, 25% over two steps.) $^1$H-NMR (360 MHz, CDCl$_3$) δ (ppm)

1470, 1444, 1374, 1280, 1251, 961, 900, 887, 838. HRMS calcd for C$_{24}$H$_{24}$N$_3$O$_3$FSiNa (M+Na$^+$) 472.1469, found (M+Na$^+$) 472.1461.

Compound 9: Compound 7 (20 mg, 0.045 mmol) and K$_2$CO$_3$ (6 mg, 0.045 mmol) were suspended in MeCN (0.5 ml). Compound 8 was added as a solution (38 mg in 0.5 ml MeCN). The resulting suspension was purged with argon and DCM (0.5 ml) and TMS-EtOH (0.2 ml) were added. The reaction was stirred at room temperature for 16 hours during which time the solution became purple. The solvent was then stripped and the crude material purified by silica gel chromatography eluting with toluene:acetone 25:1 ramping to 1:1. The desired product 9 was isolated as a purple solid (16 mg, 49%). $^1$H-NMR (500 MHz, CDCl$_3$) δ (ppm) 8.84 (dd, J=9.1, 2.3 Hz, 1H), 8.75 (t, J=2.5 Hz, 1H), 8.33 (d, J=2.5 Hz, 1H), 7.35 (d, J=8.9 Hz, 1H), 7.17 (dd, J=8.6, 2.5 Hz, 1H), 6.02 (m, 1H), 5.86 (m, 1H), 5.38 (m, 1H), 5.31 (m, 1H), 4.20 (m, 2H), 3.22 (s, 3H), 1.08, (s, 9H), 0.80 (m, 2H), 0.34 (s, 6H), 0.02 (s, 9H). $^{13}$C-NMR (125 MHz, CDCl$_3$) δ (ppm) 197.7, 170.0, 169.5, 166.3, 158.2, 156.2, 155.0, 150.5, 148.6, 143.3 (d, J$_{C-F}$=34.3 Hz), 141.9, 131.9, 124.6, 121.6 (d, J$_{C-F}$=8.5 Hz), 121.0, 119.0 (d, J$_{C-F}$=19.9 Hz), 116.1, 115.0 (d, J$_{C-F}$=109.4 Hz), 110.5 (d, J$_{C-F}$=5.4 Hz), 92.8, 85.6, 83.6, 78.4, 75.7, 64.0, 24.0, 18.6, 17.5, −1.4, −4.0. IR (thin film) ν (cm$^{-1}$)=2955, 2927, 2856, 1977, 1747, 1697, 1556, 1464, 1413, 1379, 1327, 1282, 1233, 1141, 1064, 1036, 963, 918, 840, 779, 689. HRMS calcd for C$_{36}$H$_{40}$N$_3$O$_6$FSi$_2$Ru (M$^+$) 787.1483, found (M+) 787.1487, HRMS calcd for $C_{35}H_{40}N_3O_5FSi_2Ru$ (M–CO+) 759.1534, found (M–CO+) 759.1522.

Compound 10: Compound 9 (32 mg, 0.041 mmol) was dissolved in THF (1.8 ml). The resulting solution was purged with argon and cooled to 0° C. A solution of tBAF (163 μl of a 1 M solution in THF, 0.163 mmol) was then added. The solution was stirred for one hour while warming to room temperature, during which time a black suspension formed. The reaction was then quenched by adding a 20% aqueous solution of $NH_4Cl$ followed by extraction into EtOAc (3×). The combined organic extracts were washed with 1 N HCl, $H_2O$, and brine, dried over $Na_2SO_4$, and evaporated. The crude material was then purified via silica gel chromatography eluting with toluene:acetone 5:1 ramping to 1:1 and finally adding 0.1% HOAc to the mobile phase. The desired product 10 was isolated as a purple solid (17 mg, 71%). $^1$H-NMR (500 MHz, acetone $d_6$) δ (ppm) 9.12 (t, J=2.5 Hz, 1H), 8.64 (d, J=9.4 Hz, 1H), 8.17 (d, J=2.2 Hz, 1H), 7.55 (d, J=8.7 Hz, 1H), 7.14 (dd, J=8.7, 2.4 Hz, 1H), 6.23 (d, J=1.5 Hz, 1H), 6.16 (d, J=1.4 Hz, 1H), 5.70 (t, J=1.9 Hz, 2H), 3.00 (s, 3H). $^{13}$C-NMR (125 MHz, Acetone-$d_6$) δ (ppm) 199.7, 170.0, 169.8, 167.6, 159.0, 157.0, 155.3, 148.8, 145.1 (d, $J_{C-F}$=35.2), 142.7, 132.4, 125.5, 122.0 (d, $J_{C-F}$=8.8 Hz), 118.6 (d, $J_{C-F}$=22.5 Hz), 117.2 (d, $J_{C-F}$=40.2 Hz), 116.1, 110.9 (d, $J_{C-F}$=6.3 Hz), 109.9, 92.7, 89.2, 83.8, 79.7, 78.8, 23.7. IR (thin film) ν ($cm^{-1}$)=2956, 2920, 2848, 1973, 1745, 1694, 1566, 1470, 1414, 1378, 1326, 1270, 1225, 1154, 1064, 959, 798, 670. HRMS calcd for $C_{25}H_{13}N_3O_6FRu$ (M+) 571.9832, found (M+) 571.9831.

Compound 11: Compound 10 (16 mg, 0.028 mmol) was dissolved in DMF (1.5 ml). The resulting solution was purged with argon and cooled to 0° C. To this solution was added N-hydroxy succinimide (5 mg, 0.042 mmol) and EDCI-HCl (8 mg, 0.042 mmol). The solution was stirred for 16 hours while warming to room temperature. The DMF was then stripped under high vacuum and the residue coevaporated with DCM/acetone 1/1. The crude material was purified via silica gel chromatography eluting with toluene:acetone 5:1. The desired product 11 was isolated as a purple solid (12 mg, 64%). $^1$H-NMR (500 MHz, DMSO-$d_6$) δ (ppm) 9.33 (t, J=2.5 Hz, 1H), 9.27, (s, 1H), 8.76 (dd, J=9.3, 2.3 Hz, 1H), 8.10 (d, J=2.4 Hz, 1H), 7.47 (d, J=8.7 Hz, 1H), 7.09 (dd, J=8.7, 2.5 Hz, 1H), 6.62 (d, J=1.4 Hz, 1H), 6.53 (d, J=1.2 Hz, 1H), 5.84 (m, 1H), 5.77 (m, 1H), 3.30 (s, 3H), 2.70 (s, 4H). $^{13}$C-NMR (125 MHz, DMSO-$d_6$) δ (ppm) 198.3, 169.8, 169.1, 168.9, 161.6, 157.8, 155.8, 153.9, 152.0, 146.7, 145.0 (d, $J_{C-F}$=34.7), 141.3, 131.0, 123.9, 120.7 (d, $J_{C-F}$=11.6 Hz), 117.8 (d, $J_{C-F}$=20.8 Hz), 116.3 (d, $J_{C-F}$=69.4 Hz), 114.5, 109.9 (d, $J_{C-F}$=6.9 Hz), 108.3, 93.9, 87.9, 80.7, 80.1, 72.6, 25.3, 23.5. IR (thin film) ν ($cm^{-1}$)=2920, 2854, 1981, 1768, 1739, 1694, 1555, 1454, 1415, 1372, 1327, 1276, 1204, 1075, 994, 959.

Compound 13: Compound 12 (Bregman, H., and Meggers, E. (2006) *Ruthenium half-sandwich complexes as protein kinase inhibitors: an N-succinimidyl ester for rapid derivatizations of the cyclopentadienyl moiety*, Org Lett 8, 5465-5468) (50 mg, 0.115 mmol) was dissolved in DMF (2 ml). The resulting solution was cooled to 0° C. and purged with argon. To this solution was added N-hydroxy succinimide (15 mg, 0.127 mmol) and EDCI-HCl (24 mg, 0.127 mmol). The reaction was stirred for two hours at 0° C. Then 2-amino-2-methyl-1,3-propanediol (15 mg, 0.138 mmol) was added. The reaction was stirred for 16 hours while warming to room temperature. The DMF was then evaporated under high vacuum and the resulting residue coevaporated with MeCN. This material was then carried forward crude.

Compound 14: Crude 13 was dissolved in MeCN (250 ml), purged with argon, and irradiated with a medium pressure mercury lamp (450 W) through a uranium filter for 3.5 hours. The resulting solution was purged with $CO_{(g)}$ followed by stirring under positive CO pressure for 18 hours. The solution was then concentrated to 10 ml and filtered through a short plug of basic aluminum oxide. The filtrate was concentrated yielding 14 as a yellow film (20 mg, 38% crude). This material was used crude without further purification.

Compound 15: Compound 7 (12 mg, 0.028 mmol) and $K_2CO_3$ (4 mg, 0.028 mmol) were dissolved in DCM (0.5 ml). Compound 14 was added as a solution (20 mg in 0.5 ml of MeCN). The solution was diluted with an additional 0.5 ml of MeCN. The reaction was then purged with argon and heated to 50° C. for 16 hours resulting in a purple solution. The solvent was then stripped and the crude material purified via silica gel chromatography eluting with toluene:acetone 10:1 ramping to 1:1 yielding 15 was a purple solid (4 mg, 18%). $^1$H-NMR (500 MHz, acetone $d_6$) δ (ppm) 9.29 (t, J=2.5 Hz, 1H), 8.79 (dd, J=9.3, 2.3 Hz, 1H), 8.35 (d, J=2.4 Hz, 1H), 7.58 (d, J=8.8 Hz, 1H), 7.16 (dd, J=8.7, 2.5 Hz, 1H), 6.71 (s, 1H), 6.27 (m, 1H), 6.16 (m, 1H), 5.57 (m, 2H), 4.10 (s, 2H), 3.42 (m, 4H), 3.16 (s, 3H), 1.08 (s, 9H), 0.96 (s, 3H), 0.33 (s, 6H). $^{13}$C-NMR (125 MHz, Acetone-$d_6$) δ (ppm) 200.2, 170.3, 170.1, 165.3, 159.2, 157.3, 155.7, 150.8, 149.6, 145.8 (d, $J_{C-F}$=34.7), 142.7, 132.4, 125.4, 122.1 (d, $J_{C-F}$=11.6 Hz), 121.2, 118.8 (d, $J_{C-F}$=23.1 Hz), 117.0, 116.3, 114.8, 111.6 (d, $J_{C-F}$=5.8 Hz), 90.3, 88.1, 85.6, 81.9, 77.7, 66.4, 66.3, 60.4, 26.4, 23.9, 19.1, 19.0, −4.0. IR (thin film) ν ($cm^{-1}$)=3373, 2926, 2847, 1971, 1748, 1696, 1644, 1563, 1462, 1414, 1378, 1326, 1234, 1063, 963, 916, 840. HRMS calcd for $C_{35}H_{37}N_4O_7FSiRu$ (M+) 774.1459, found (M+) 774.1429.

Compound 16: Compound 15 (4 mg, 0.005 mmol) was dissolved in THF (0.5 ml). The resulting solution was purged with argon and tBAF was added (7 μl of a 1M solution in THF, 0.007 mmol). The reaction was stirred for 30 minutes and was then quenched with HOAc. The solvent was then evaporated and the crude material purified by silica gel chromatography eluting with toluene:acetone 5:1 ramping to 1:1 providing 16 as a purple solid (2 mg, 61%). $^1$H-NMR (500 MHz, acetone $d_6$) δ (ppm) 9.28 (t, J=2.6 Hz, 1H), 8.77 (dd, J=9.4, 2.3 Hz, 1H), 8.24 (d, J=2.5 Hz, 1H), 8.16 (s, 1H), 7.53 (d, J=8.7 Hz, 1H), 7.16 (dd, J=8.7, 2.5 Hz, 1H), 6.79 (s, 1H), 6.30 (m, 1H), 6.20 (m, 1H), 5.55 (m, 2H), 4.17 (s, 2H), 3.42 (m, 4H), 3.16 (s, 3H), 0.96 (s, 3H). $^{13}$C-NMR (125 MHz, DMSO-$d_6$) δ (ppm) 199.6, 169.2, 169.0, 163.2, 157.6, 155.7, 153.7, 151.9, 146.9, 144.88 (d, $J_{C-F}$=32.4), 141.1, 130.9, 123.9, 120.5 (d, $J_{C-F}$=16.2 Hz), 117.1 (d, $J_{C-F}$=20.8 Hz), 116.3 (d, $J_{C-F}$=20.8 Hz), 114.5, 109.4, 108.3, 90.1, 87.2, 84.1, 80.2, 78.4, 63.1, 59.0, 23.5, 17.9. IR (thin film) ν ($cm^{-1}$)=3321, 2923, 2855, 1967, 1745, 1694, 1632, 1555, 1442, 1413, 1376, 1325, 1270, 1225, 1061, 958. HRMS calcd for $C_{29}H_{23}N_4O_7FClRu$ (M+Cl−) 695.0283, found (M+Cl−) 695.0317.

Separation of enantiomers of 16: A 2 mg sample of 16 was dissolved in EtOH and diluted with an equal volume of hexanes. The solution was then injected onto a chiral HPLC column (Daicel Chiralpak 1B) and eluted with Hex:EtOH at 70%:30% ramping to 40%:60% over 20 minutes with a flow rate of 0.6 ml/min. Up to 100 μl injections were possible while still achieving base-line separation. In order to verify the separation was successful, circular dichrosim (CD) spectra were measured for each enantiomer of 16.

Figure 11:
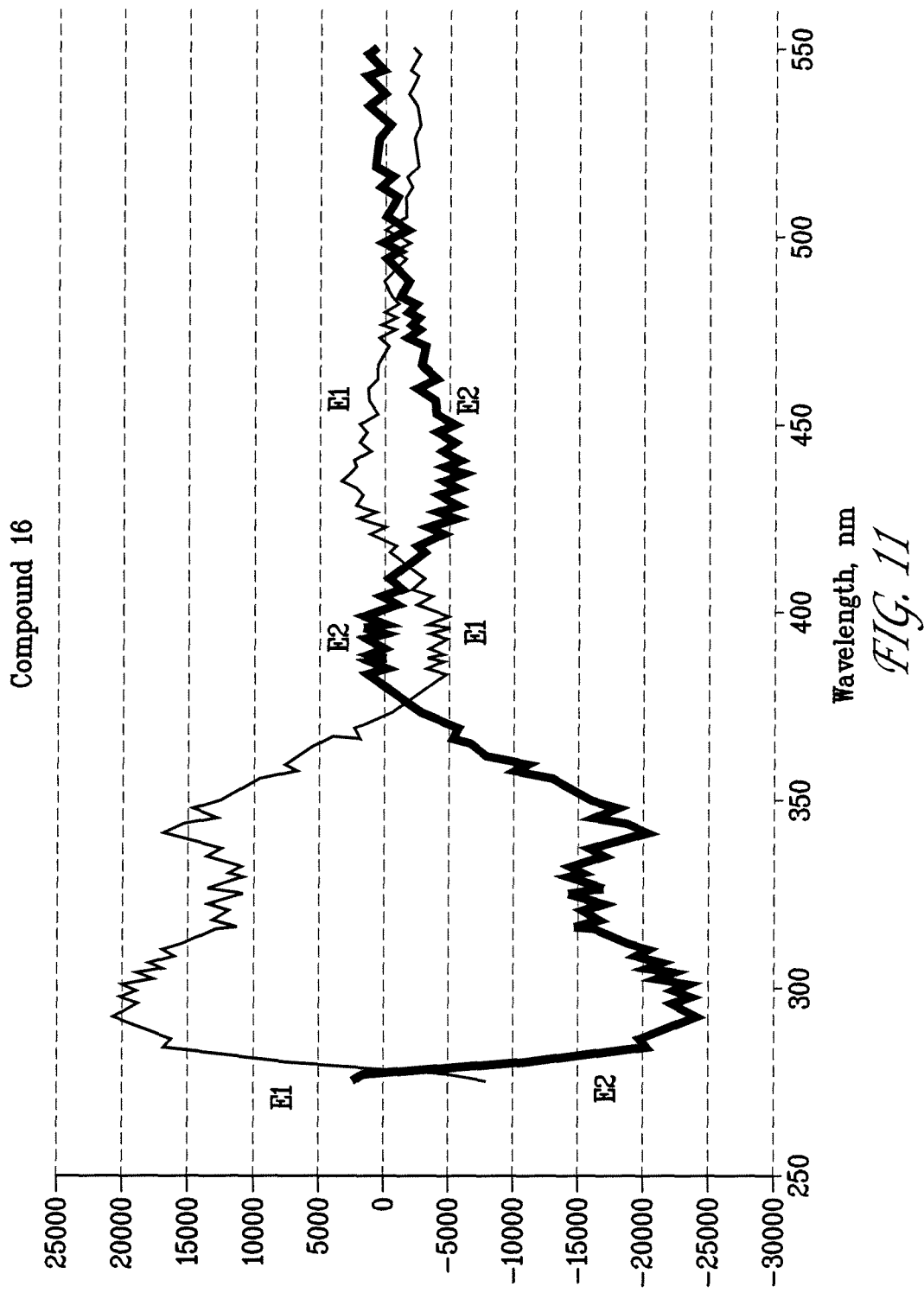
FIG. 11 shows CD spectra of 16E1 (E5E1) and 16E2 (E5E2) measured in DMSO.

The resulting spectra are shown in FIG. 11.

Scheme III-Library Synthesis

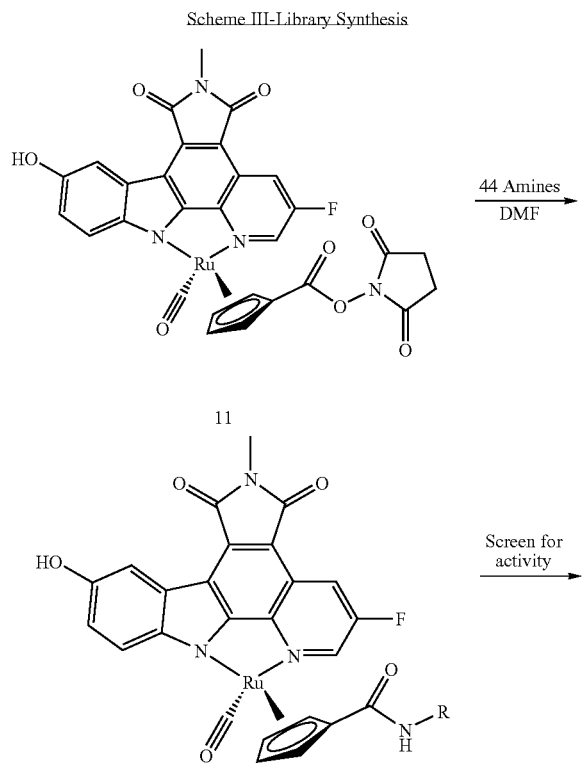

The library was prepared in a 96-well plate. Initially 8 µl of DMF was distributed to 44 wells of the well plate. This was followed by the addition of 10 µl of a 4 mM stock solution of 11 in DMF to each of these wells. Finally 2 µl of a 100 mM stock solution (also in DMF) of 44 different amines was added to each well. This gives a total reaction volume of 20 µl with a substrate concentration of 2 mM and an amine concentration of 10 mM. The wells were mixed via a multi-channel pippett and then left at room temperature overnight. Reaction completion was verified for random wells by TLC analysis (Hec:EtOAc 1:3). The wells were then diluted to the desired screening concentration and screened against the target kinase PI3K.

Example 2

In Vitro Kinase Assays

BRAF kinase assay—Recombinantly expressed GST-MEK diluted in TTBS buffer (20 mM Tris pH 7.5, 150 mM NaCl, 0.05% TWEEN-20) to 50 µg/mL in a volume of 100 µL was bound to the wells of a 96-well glutathione coated plate (Pierce Biotechnology). 1 µL of compound with 2× serial dilutions in a 100% DMSO stock solution were added to a mixture of 50 µL of a buffer containing 50 mM HEPES pH 7.0 with 0.7 pmoles of BRAF kinase. This mixture was incubated at room temperature for 1 hour before it was added into the GST-MEK bound wells of the 96-well plate. An additional 50 µL of phosphorylation buffer (50 mM HEPES pH 7.0, 200 mM NaCl, 10 mM MgCl$_2$, 200 µM ATP) was added into the well mixture to start the kinase reaction at 37° C. for 30 min with intermittent shaking. The kinase reaction was stopped by extensive washing with TTBS buffer and a 1:5000 dilution of Anti-phospho-MEK1 (Ser218/222)/MEK2 (Ser222/226) monoclonal antibody (Millipore) in TTBS was subsequently added into the wells and incubated for 1 hour with shaking. Goat Anti-Rabbit IgG (H+L)-HRP Conjugate (BioRad Laboratories) in a 1:5000 dilution was added into the wells to incubate at room temperature with shaking. Finally, the SuperSignal ELISA Pico chemiluminescent substrate (Pierce Biotechnology) was added into the wells. The luminescence signal was recorded with a luminescence filter using a Wallac 1420 luminometer (PerkinElmer). These data were processed and IC$_{50}$ values were derived from fitting into a sigmoidal dose response model using GraphPad Prism.

MST1 kinase assay—Kinase assays were performed using labeled γ-P$^{32}$ ATP and the incorporation of labeled phosphate onto the substrate FOXO was monitored. Kinase assays were performed using kinase buffer containing 10 mM Tris pH 7.5, 10 mM MgCl$_2$, 1 mM dithiothreitol (DTT), 1 mM phenylmethylsulfonyl fluoride (PMSF) and a cocktail containing phosphatase inhibitor. 5 µCi of labeled γ-P$^{32}$ ATP and a final concentration of 200 µM of ATP were used for each reaction. 10 nM of the enzyme was pre-incubated for 30 min with various concentrations of inhibitor and an equivalent amount of DMSO was used as a control. After 30 min of incubation of the enzyme with the inhibitor, 1 µg of substrate was added. The reaction was initiated by addition of ATP. All reactions were incubated at 37° C. for 30 min. and then stopped with SDS gel-loading dye; subsequently samples were heated for 3 min and loaded onto a 16% Tris-glycine gel (Novagen). The bands were visualized using high sensitivity Kodak film and the results were quantified using the software ImageJ.

PAK1 kinase assay—Kinase assays were performed using labeled γ-P$^{32}$ ATP and the incorporation of labeled phosphate onto the myelin basic protein (MBP) substrate was monitored. Different concentrations of compound inhibitor were incubated with 0.1 nM PAK1 kinase in 20 mM MOPS pH 7, 30 mM MgCl$_2$, 1 mM EDTA, 0.8 µg/µL bovine serum albumin, 5% DMSO (resulting from the inhibitor stock solution), in the presence of 25 µg of MBP substrate for 20 minutes. Reactions were initiated by adding ATP to a final concentration of 1 µM including 0.2 µCi/µL γ-$^{32}$P ATP to a final volume of 25 µL. The reactions were terminated by spotting 17.5 µL onto a circular P81 phosphocellulose paper (diameter 2.1 cm), followed by washing three times with 0.75% phosphoric acid and one time with acetone. The dried P81 papers were transferred to scintillation vials and 4 ml of scintillation cocktail was added. The counts per minute (CPM) were measured with a scintillation counter and the enzyme activity in the presence of the inhibitor was calculated as a percentage of the control sample corrected by the background.

PIM1 kinase assay—Kinase assays were performed using labeled γ-P$^{32}$ ATP and the incorporation of labeled phosphate onto substrate (S6 kinase/Rsk2 peptide) was monitored. Various concentrations of inhibitor were incubated at room temperature in 20 mM MOPS, 30 mM MgCl2, 0.8 µg/µl BSA, 5% DMSO (resulting from the inhibitor stock solution), pH 7.0, in the presence of substrate (S6 kinase/Rsk2 Substrate Peptide 2: 50 µM) and PIM1 kinase (0.02 ng/µl). After 15 min, the reaction was initiated by adding ATP to a final concentration of 100 µM, including approximately 0.2 µCi/µl γ-P$^{32}$ ATP. Reactions were performed in a total volume of 25 µL. After 30 minutes, the reaction was terminated by spotting 17.5 µL on a circular P81 phosphocellulose paper (diameter 2.1 cm, Whatman) followed by washing four times (five minutes each wash) with 0.75% phosphoric acid and once with acetone. The dried P81 papers were transferred to a scintillation vial and 5 ml of scintillation cocktail were added and the counts per minute (CPM) determined with a Beckmann 6000 scintillation counter. IC50 values were defined to be the concentration of inhibitor at which the CPM was 50% of the control sample, corrected by the background.

GSK3α kinase assay—The procedure was as described for the PIM1 kinase assay, but in the presence of substrate peptide phospho-glycogen synthase peptide-2 (20 µM), and GSK3α (0.2 or 0.4 ng/µl for IC50 determinations).

Example 3

Compound Screening and Characterization

Figure 7:
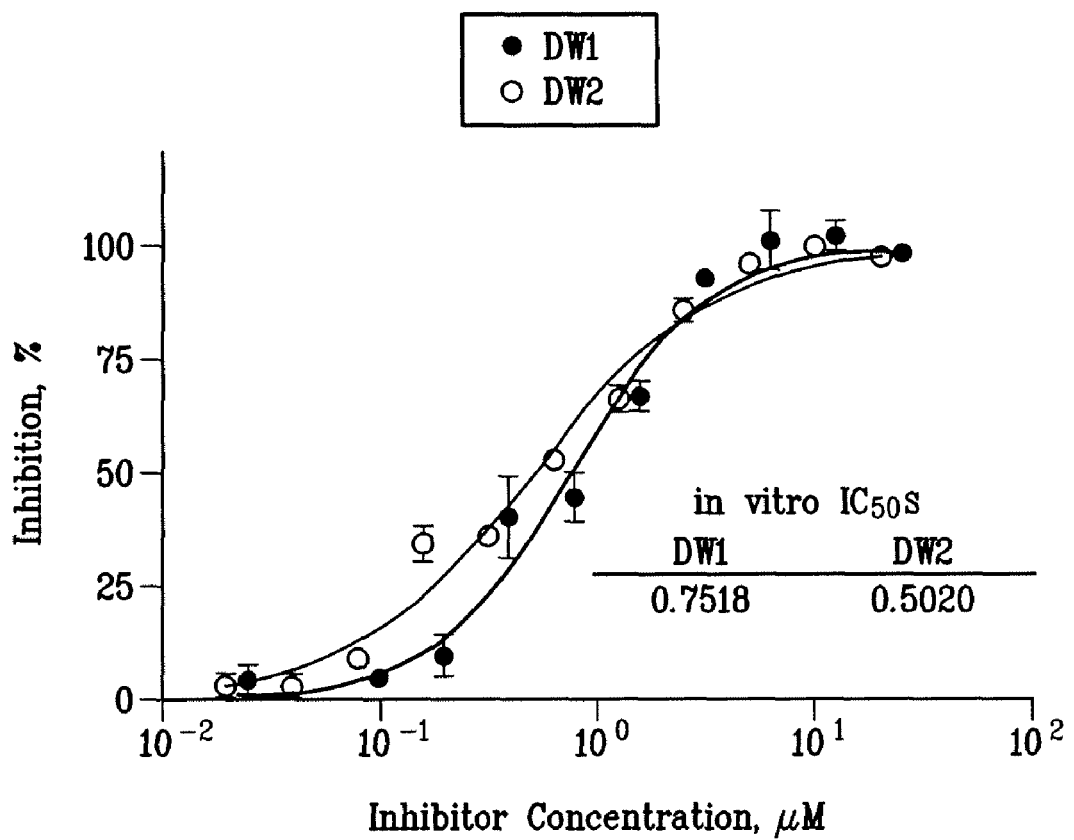
FIG. 7 shows dose response curves of DW1 and DW2 inhibitors against PI3Kγ. $IC_{50}$ values were derived by fitting the data to a sigmoidal dose-response (variable slope) model in GraphPad Prism.

A library of 75 compounds (20, 25) with a diverse configuration of ligands around a ruthenium metal (FIG. 1A) were screened against the human PI3Kα isoform using a fluorescence polarization-based kinase assay (Echelon Biosciences). From this library, we identified the racemic compound DW12, which bears an additional hydroxyl group on the indole group as the most potent compound with an IC50 value of around 1 µM using a Kinase Glo assay (FIG. 1A, FIG. 7). DW12 is also known to be a highly potent inhibitor for the protein kinases GSK3 (24) and PIM1 (21).

In order to understand its mode of inhibition and to provide a structural platform for structure-based inhibitor optimization to improve potency as well as selectivity, one enantiomer, named DW2, was cocrystallized with human PI3Kγ. The PI3Kγ/DW2 cocrystals formed in the space group C2 with one protein/inhibitor complex per asymmetric unit cell, and the structure was determined by molecular replacement using the human unliganded PI3Kγ structure as a search model. The strong electron density signal of the ruthenium atom and the proximal outline of the inhibitor allowed for the unambiguous placement of the DW2 inhibitor into the PI3Kγ active site (FIG. 1B). The structure was refined to 2.8 Å resolution to excellent refinement statistics and geometrical parameters (Table 1).

TABLE 1

Statistics of crystallographic data collection and structural refinement.

| Data collection | | |
|---|---|---|
| Beamline | APS 23ID-D | NSLS X6A |
| Complex | PI3Kγ-DW2 | PI3Kγ-E5E2 |
| Space group | C2 | C2 |
| Cell dimensions | | |
| a, b, c (Å) | 143.6, 68.1, 106.3 | 145.1, 68.3, 107.0 |
| β (°) | 95.26 | 95.14 |
| Number of unique reflections | 24,815 | 18,708 |
| Resolution (Å) | 50-2.8 | 50-3.2 |
| $R_{merge}{}^{a,b}$ | 0.054 (0.423) | 0.065 (0.608) |
| I/σ(I) | 24.7 (2.3) | 19.7 (2.0) |
| Completeness (%) | 97.3% (80.2%) | 99.2% (98.9%) |
| Multiplicity | 4.8 (3.6) | 3.8 (3.8) |
| Refinement | | |
| $^{c}R_{work}/^{d}R_{free}$ | 25.2%/28.7% | 26.5%/30.5% |
| RMSD | | |
| Bond lengths (Å) | 0.012 | 0.012 |
| Bond angles (°) | 1.71 | 1.55 |

$^{a}$Highest resolution shell is shown in parentheses.
$^{b}R_{merge} = \Sigma_{hkl}|I(hkl) - <I(hkl)>|/\Sigma_{hkl}(hkl)$, where $<I(hkl)>$ is the mean of the symmetry-equivalent reflections of I(hkl)
$^{c}R_{work} = \Sigma||F_o| - |F_c||/|F_o|$
$^{d}R_{free} = \Sigma_T||F_o| - |F_c||/\Sigma_T|F_o|$ (where T is a test data set of 9.3% of the total reflections randomly chosen and set aside before refinement)

Overall, the protein component of the PI3Kγ/DW2 structure adopts the same conformation as the unliganded PI3Kγ protein and the conservation of the overall structure suggests that the organoruthenium inhibitor binds to the PI3Kγ ATP binding pocket without significant alteration of the native PI3Kγ conformation (FIG. 1C).

Figure 1E:
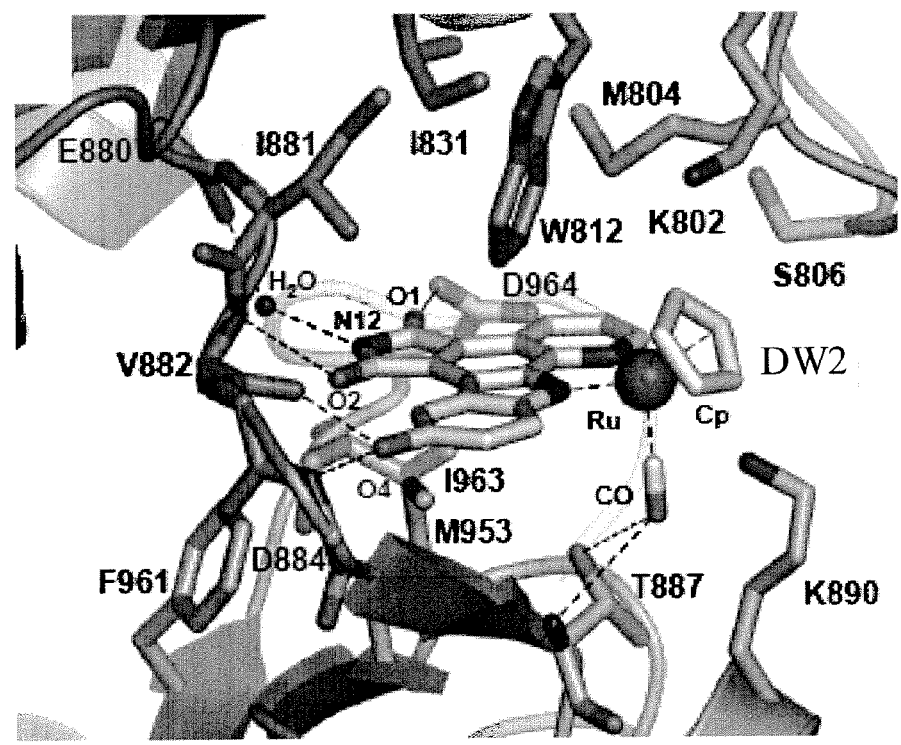
Figure 1F:
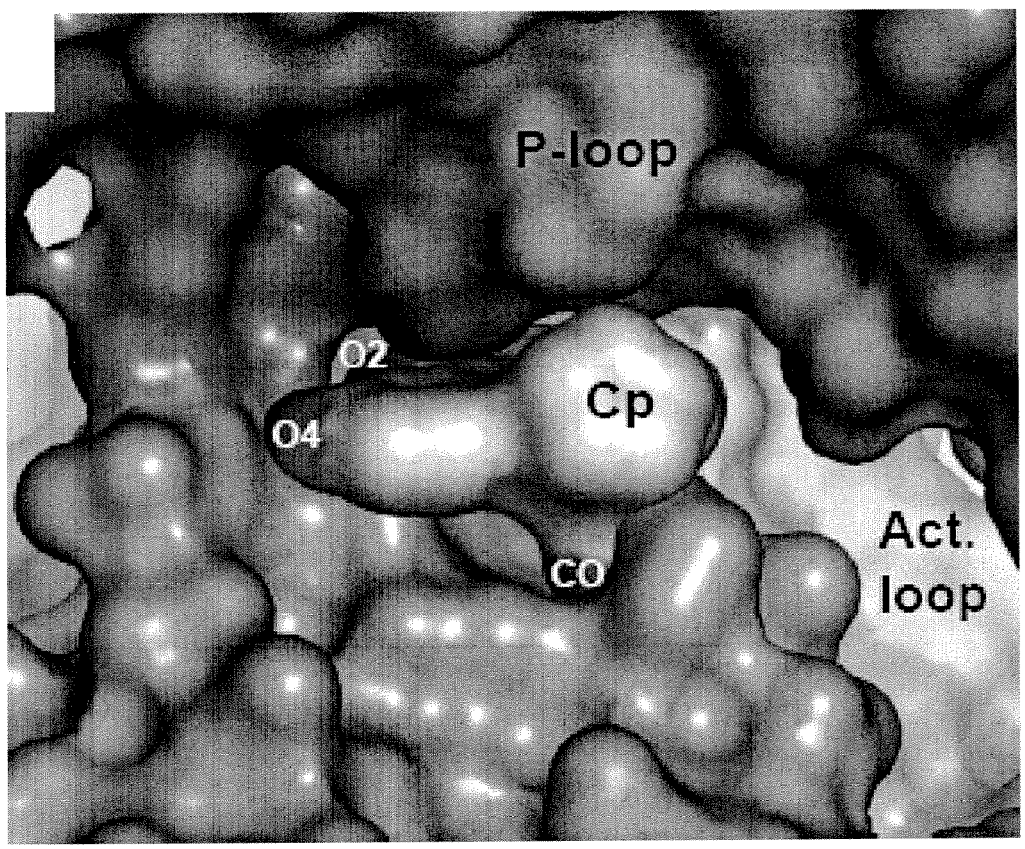

Detailed view of the interactions between the PI3Kγ kinase domain and DW2. As designed, the DW2 inhibitor occupies the ATP binding pocket of the kinase domain with about a 2.4 Å displacement towards solvent of the DW2 inhibitor relative to ATP (FIG. 1D). The maleimide moiety of the DW2 inhibitor largely overlaps with the adenosine moiety of ATP. The DW2 maleimide moiety and derivatized pyridocarbazole makes extensive hydrogen bonding interactions with both protein side chain and main chain atoms of the PI3Kγ kinase domain (FIG. 1E). In particular, the N12 atom of the maleimide nitrogen forms water mediated hydrogen bonds with the main chain carbonyl of residue Glu880; and the DW2 carbonyl oxygens, O1 and O2, of the maleimide moiety form hydrogen bonding interactions with the side chain oxygen of residue Glu964 and the main chain amide nitrogen of residue Val882, respectively. The O4 atom of the DW2 phenol moiety also hydrogen bonds to the main chain carbonyl of Val882 and main chain amide of residue Asp884. Several van der Waals contacts stabilize the interaction between PI3Kγ and DW2 including contacts between the inhibitor ring system with the side chains of residues Trp812, Met953, Ile881, Ile831, Met804, Ile963, Thr887, Val882, Phe961 and Ser806. The ruthenium coordination center of the DW2 inhibitor adopts a pseudo-tetrahedral geometry with the CO ligand pointing towards the C-lobe of the kinase domain and the cyclopentadiene (Cp) ligand pointing to the P-loop of the kinase. The CO ligand of the ruthenium makes hydrogen bonding contacts with the main chain amide nitrogen and side chain hydroxyl of residue Thr887, while the Cp ligand of the ruthenium makes van der Waals contacts with the aliphatic portions of Lys890 and Lys802. A surface representation of the DW2 inhibitor shows favorable shape complementarity with the ATP binding pocket of PI3Kγ, further supporting the favorable binding properties of the DW2 inhibitor with PI3Kγ (FIG. 1F).

Figure 2A:
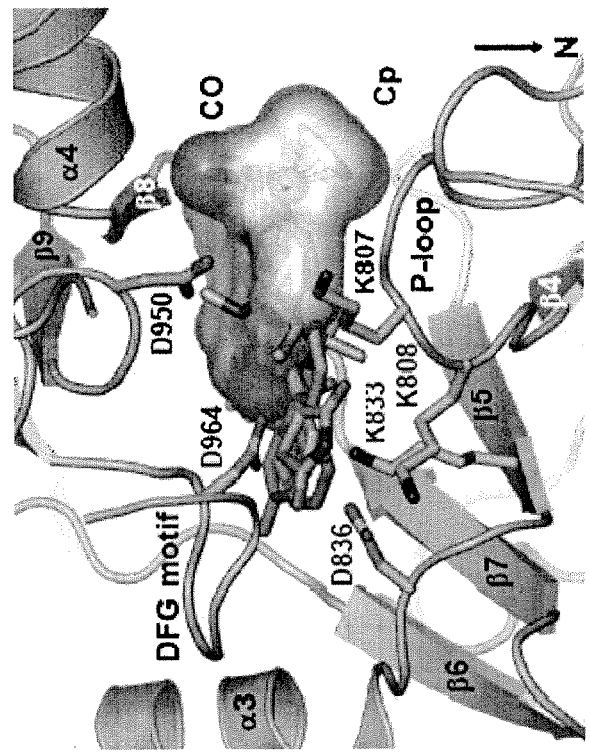
FIG. 2 illustrates the structure based design of optimized inhibitor and structure activity relationship correlation.
Figure 2B:
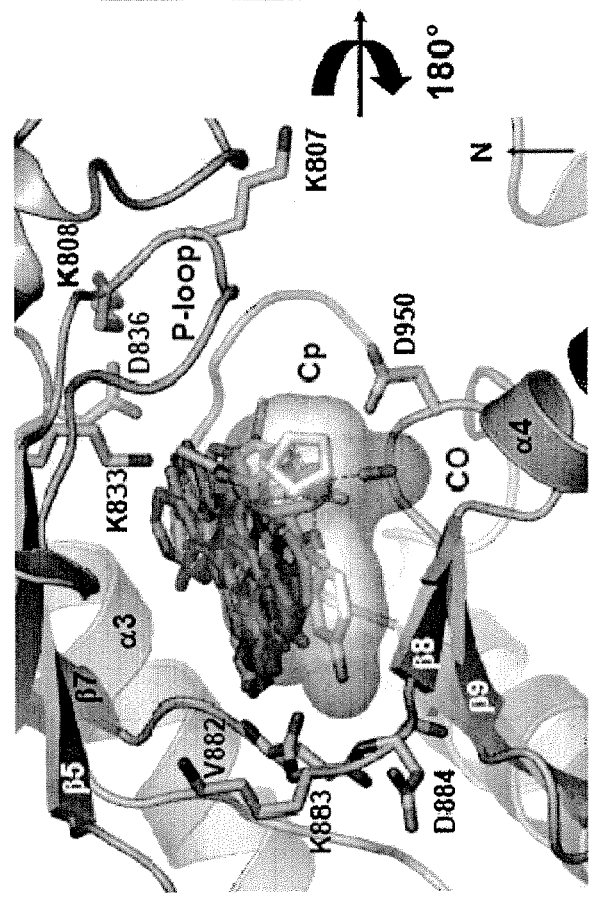
Figure 2C:
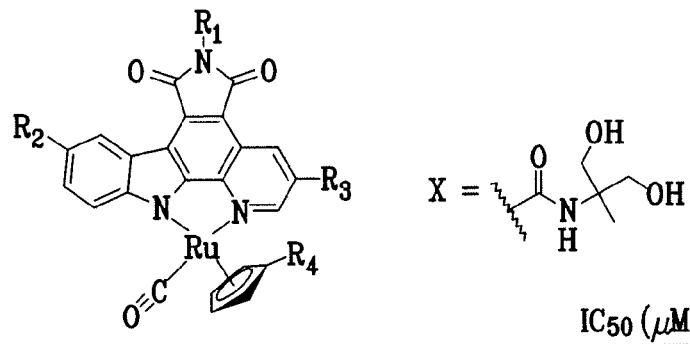
Figure 2D:
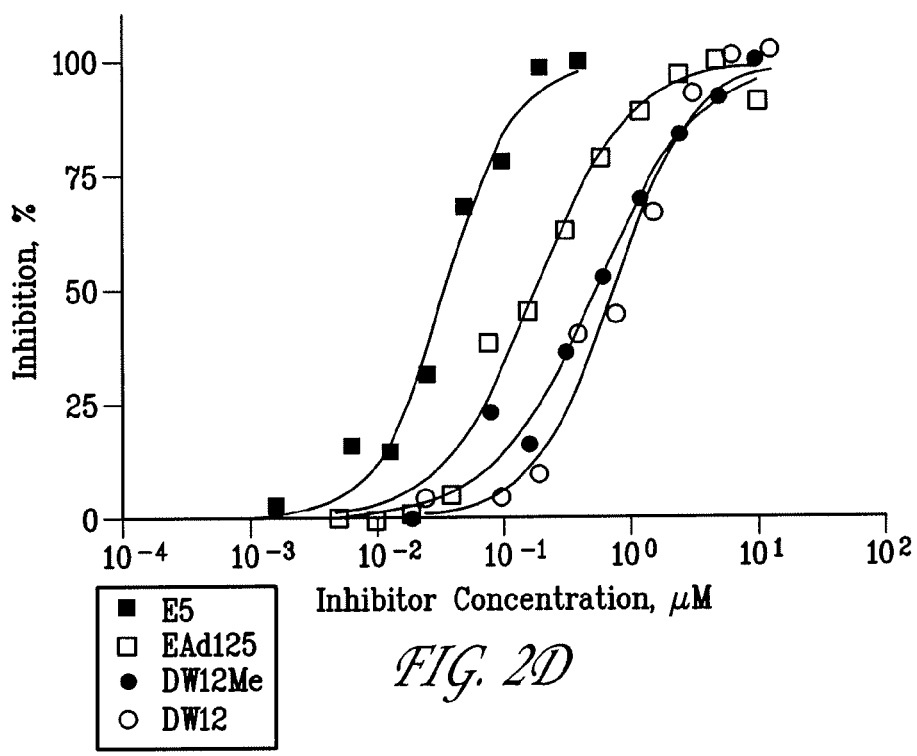

Structure based design of second generation PI3K inhibitors. A superposition of the PI3Kγ/DW2 structure with previously determined PI3Kγ structures with conventional organic inhibitors such as staurosporine, myricetin, LY294002 (26), AS605240 (27) and PIK90 (28), reveals some unique features underlying the binding of DW2 to PI3Kγ. While the maleimide, pyridine and indole moieties of the DW2 inhibitor largely overlap with other inhibitors, the phenol moiety extends into a hinge region between the N-lobe and C-lobe of the kinase domain, representing a novel region of PI3K "inhibitor space" (FIG. 2A). The observation that the phenol ring of DW2 makes complementary interactions with the PI3K active site is particularly interesting, since the HB12 homologue missing this hydroxyl group does not inhibit PI3K at a comparable inhibitor concentration (FIG. 2C). This structural evidence suggests that this phenol moiety of DW2 be retained in a subsequent round of inhibitor optimization.

The DW2 inhibitor appeared to be pushed out of the ATP binding pocket relative to the other inhibitors (FIG. 2A). This causes the maleimide nitrogen of DW2 to be too far away to directly contact the protein within the ATP binding pocket. Instead, the maleimide nitrogen makes water mediated hydrogen bonding interactions with the protein backbone. This finding is in contrast to the previous co-crystal structure of organoruthenium inhibitors with similar scaffolds in complex with protein kinases such as GSK3 (unpublished data) and PIM1 (21), in which the maleimide nitrogen is in direct contact with the protein pocket, leaving essentially no space for additional modification on the imide nitrogen. Based on this observation, it was hypothesized that a derivatization of the maleimide nitrogen, preferably to a hydrophobic group to complement a largely hydrophobic protein pocket in this region, might enhance protein interaction as well as improve kinase selectivity towards PI3K. Indeed, a slight enhancement in inhibitory potency was observed for PI3K going along with a dramatic improvement in selectivity, when a methyl group was introduced on the maleimide nitrogen (FIG. 2C).

An overlay of DW2 with other PI3K inhibitors also shows that the other inhibitors occupy an overlapping region of PI3K inhibitor space that is not occupied by the DW2 inhibitor. In particular, the other PI3K inhibitors occupy a tunnel like pocket (called pocket A hereafter) that extends into a space underneath the P-loop which is further defined by the α3 helix, the β4-β7 strands and the DFG motif of the activation loop (FIG. 2B). We attempted to derivatize the pyridine moiety which is placed in proximity to pocket A. Intriguingly, a fluorine substitution on the 3' position of pyridine moiety (EAd125) significantly increased its inhibitory potency against PI3K (FIG. 2C).

Figure 8:
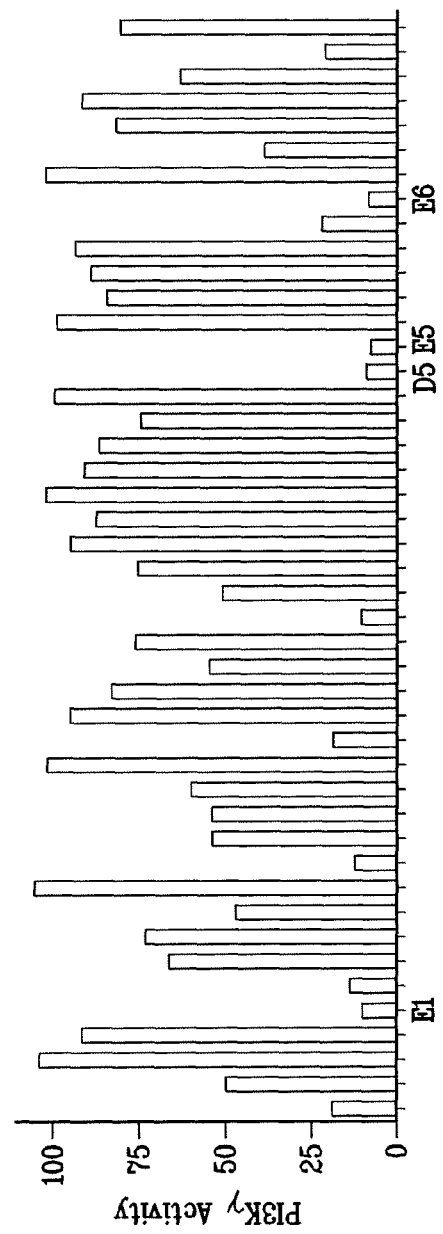
FIG. 8 provides a summary of PI3Kγ inhibition using a library of 44 derivatives on the Cp group of EAd125; compounds were assayed at a final concentration of 400 nM in 2% DMSO; $IC_{50}$ values were derived from dose response curve fitting of the Kinase-Glo assay data. R represents derivatizing groups and E denotes the original EAd125 scaffold.
Figure 8:
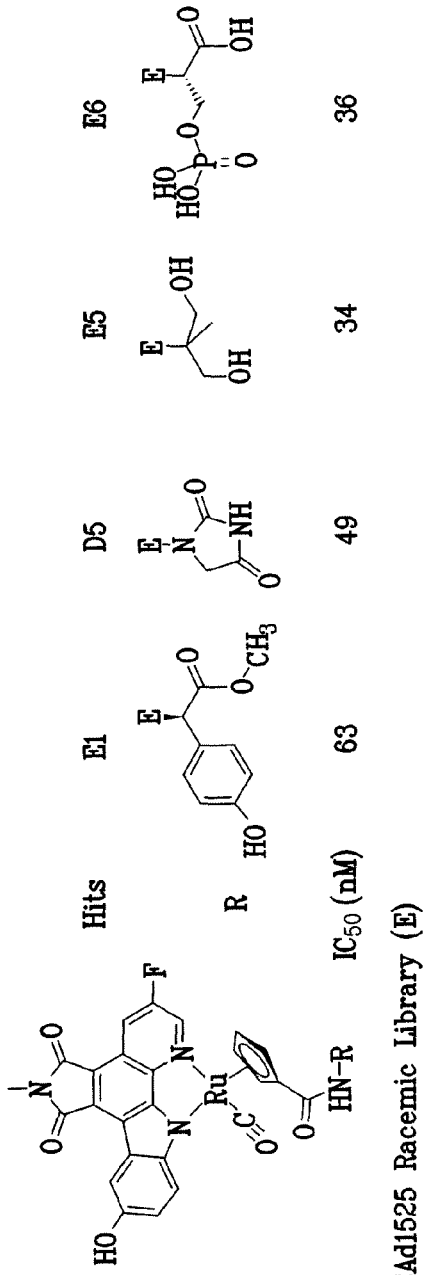

The Cp and CO ligands of the ruthenium atom occupy a novel region of PI3K inhibitor space relative to other PI3K inhibitors and serves to cap off the relatively hydrophobic PI3Kγ ATP binding pocket from solvent (FIG. 2B). The proximity of the Cp group to solvent suggests that more hydrophilic capping groups might enhance inhibitor binding. An exhaustive screening against a library of compounds with modifications on the Cp ligand of the parental EAd125 compound revealed several compounds that contained hydrogen bonding donors in this region of the molecule (FIG. 8).

Figure 3A:
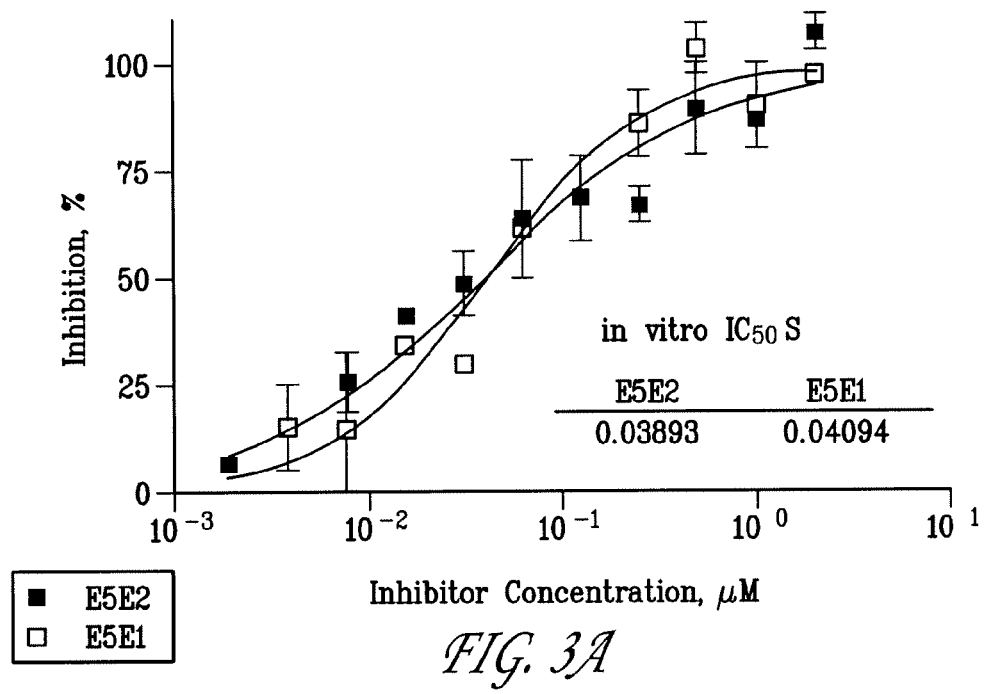
FIG. 3 provides data from the analysis of E5E2's activity for PI3K and a kinase specificity screen.

The most potent compounds from this series of DW2 analogues, E5, was separated into the pure enantiomers, named E5E1 and E5E2, and the PI3Kγ inhibition properties of these enantiomers were characterized. As illustrated in FIG. 3A, E5E1 and E5E2 displayed comparable IC50 values of 41 nM and 39 nM, respectively.

Figure 3B:
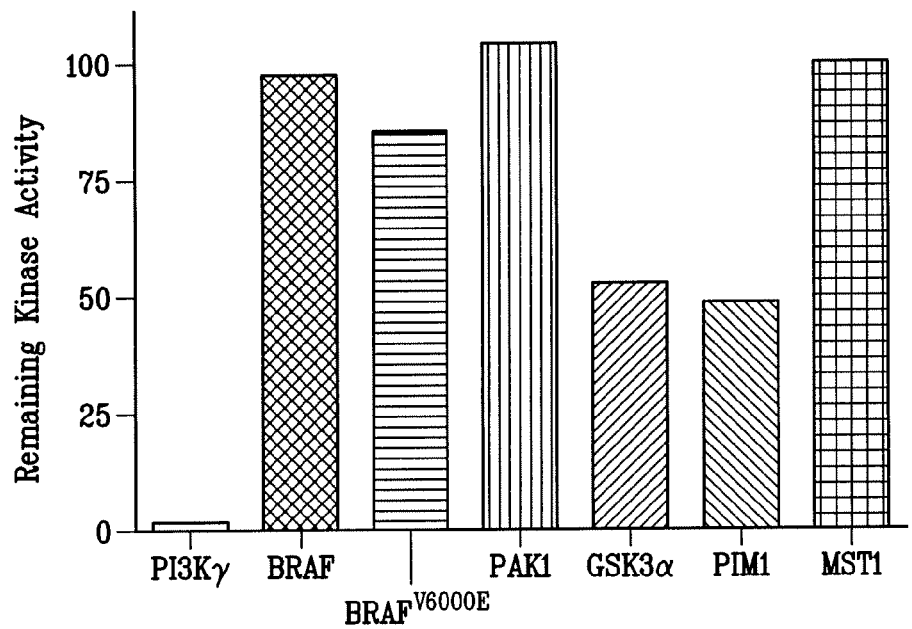
Figure 9:
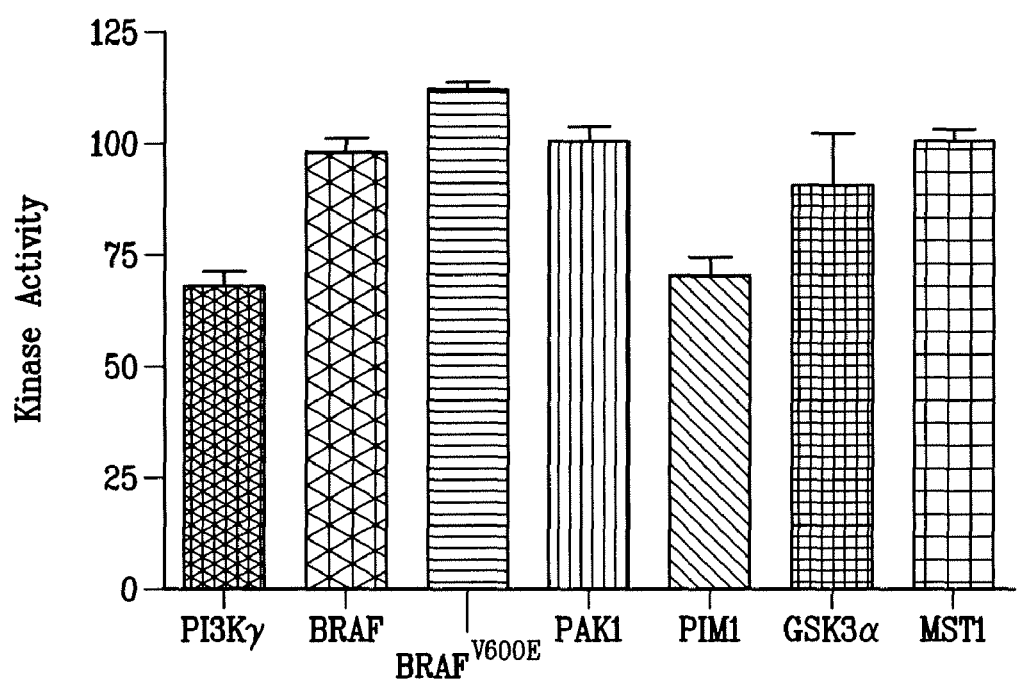
FIG. 9 illustrates the results of a PI3K and kinase specificity screen against LY294002; activity of the human PI3Kγ, MST1, $BRAF^{WT}$, $BRAF^{V600E}$, PAK1, GSK3α and PIM1 kinases at a final LY294002 concentration of 4 μM; data show mean of three independent experiments +/–s.e. mean.

Kinase specificity of the E5E2 inhibitor. In order to further characterize the role of methylation of the maleimide nitrogen on this new class of organoruthenium inhibitor's in mediating inhibition of the PI3K lipid kinases over protein kinases, we assayed the E5E2 inhibitor against five human protein kinases (MST1, PAK1, BRAF$^{WT}$ and BRAF$^{V600E}$, GSK3α and PIM1) representing four major kinase families of STE, TKL, CMGC and CAMK, respectively. This kinase panel screen revealed that the E5E2 inhibitor had significant selectivity towards PI3K over these protein kinases. In particular, the E5E2 inhibitor did not show appreciable inhibition for BRAF$^{WT}$, BRAF$^{V600E}$, PAK1 and MST1 and only showed about 50% inhibition towards the GSK3α and PIM1 kinases at an inhibitor concentration of 4 µM (FIG. 3B). Together, these results reveal that the E5E2 inhibitor exhibits nearly a 100 fold selectivity for PI3Kγ over these representative protein kinases. The selectivity of E5E2 is quite remarkable considering that GSK3α and PIM1 are common targets for this class of organoruthenium inhibitors (23, 24, 29, 30). For comparison, a previously characterized PI3K inhibitor, LY294002 (15), was assayed against the same panel of kinases used in this study (FIG. 9; data show mean of three independent experiments +/-s.e. mean). Interestingly, it was found that LY294002 was both less potent against PI3Kγ and less specific for PI3Kγ relative to the other kinases profiled in this study (compare FIGS. 3B and 9).

Figure 4A:
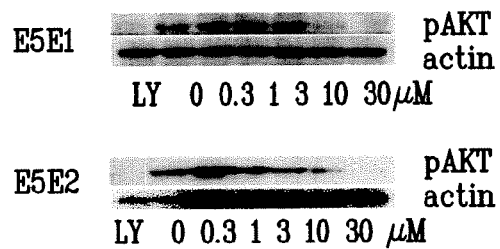
FIG. 4 provides data pertaining to the ability of E5E1 and E5E2 to inhibit PI3K activity in vivo.
Figure 4B:
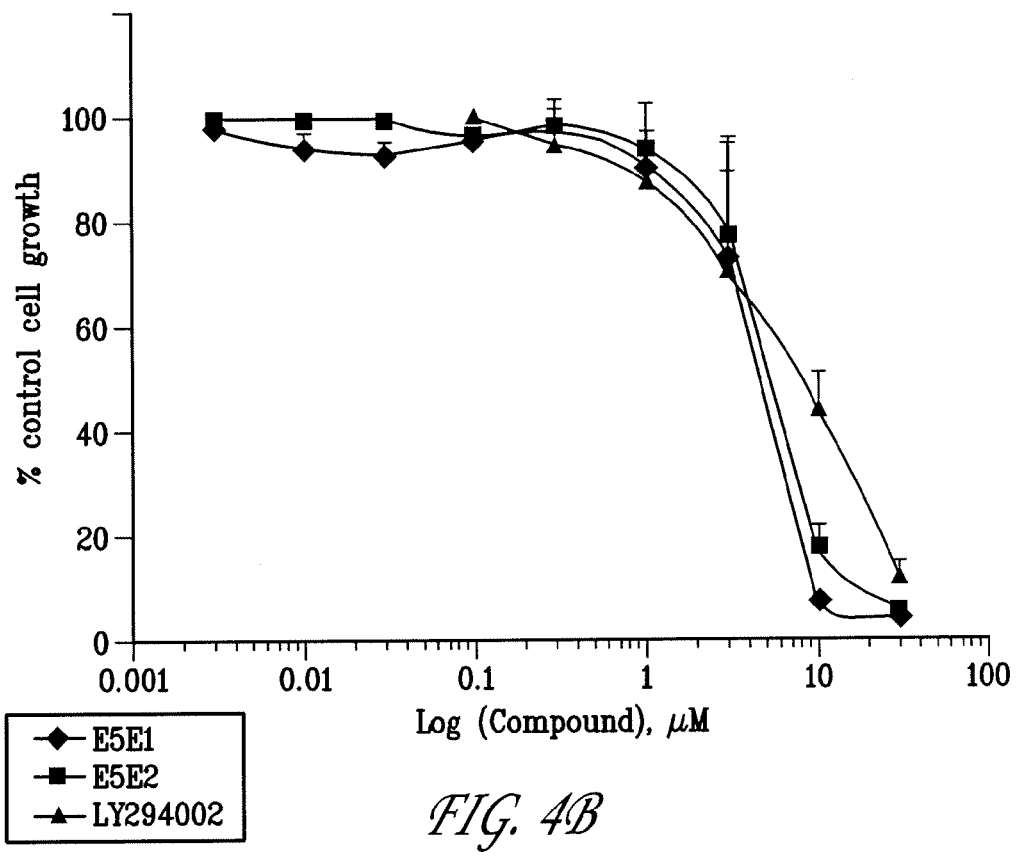
Figure 4C:

Cellular Activity of E5E1 and E5E2. Melanomas are a tumor known to have high constitutive activity in the PI3K/AKT pathway (31, 32). To probe E5E1 and E5E2's ability to inhibit proliferation of melanoma cells, the cellular response of E5E1 and E5E2 in a melanoma cell line was examined. It was found that both E5E1 and E5E2 were able to block the constitutive activity of AKT in a concentration dependent manner (FIG. 4A). Similar levels of phospho-AKT inhibition were also seen following treatment with the PI3K inhibitor LY294002 (30 µM). Inhibition of the PI3K pathway in melanoma is also known to inhibit cell growth in 2D cell culture (33). In agreement with these findings, treatment of the 1205Lu melanoma cell line with increasing concentrations of E5E1, E5E2 and LY294002 was associated with an inhibition of cell proliferation (FIG. 4B). There appeared to be a close correlation between the concentrations of E5E1/E5E2 required to inhibit phospho-AKT and those required to inhibit proliferation. In 3D cultures of melanoma cells, infection with an adenovirus encoding for a dominant negative construct of PI3K is known to block cell migration (33). In agreement with these previous results, it was found that the invasion of melanoma cells grown as 3D collagen-implanted spheroids, could be completely blocked following treatment with either E5E1 or E5E2 (both 30 µM) (FIG. 4C). Taken together, these results show that the PI3K inhibitor E5 works both in vitro and in vivo.

Figure 5A:
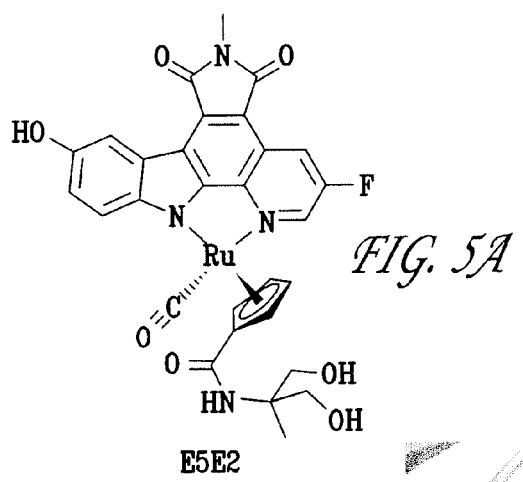
FIG. 5 depicts analyses of the structure of the E5E2 inhibitor in complex with PI3Kγ.
Figure 5B:
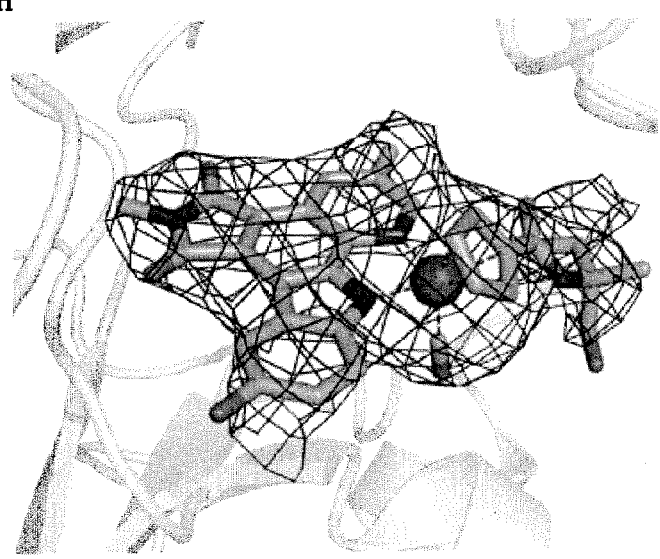

Crystal structure of PI3Kγ in complex with E5E2. To understand the structural basis for selective PI3Kγ inhibition by E5E2 (FIG. 5A) and also to confirm the design strategies inferred from structural information of the PI3Kγ/DW2 complex, the PI3Kγ/E5E2 complex was co-crystallized and its structure determined by molecular replacement with the PI3Kγ extracted from the PI3Kγ/DW2 complex as a search model. The refined structure in the absence of the E5E2 inhibitor showed strong difference electron density for the inhibitor allowing for the unambiguous modeling of the inhibitor into the ATP binding site of PI3Kγ (FIG. 5B). The E5E2 inhibitor showed more clearly defined electron density than the DW2 inhibitor and also refined to lower B-factors, consistent with the more potent PI3Kγ inhibition of the E5E2 inhibitor relative to DW2. An overlay of the E5E2 and DW2 inhibitors in the PI3Kγ active site reveals that the two inhibitors bind in almost identical positions except that E5E2 is bound about 0.7 Å more deeply in the active site pocket than DW2 (FIG. 5C).

Figure 5C:
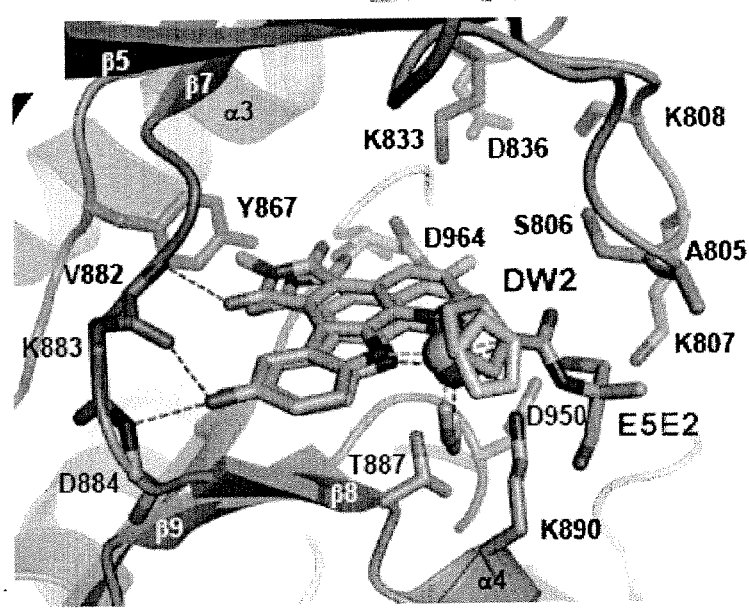

A detailed analysis of the PI3Kγ/E5E2 complex shows that the hydroxyl group of the ring system mediates hydrogen bonding interactions with the Val882, Asp884 and Ala885 main chain atoms that are analogous to the interactions that are mediated by the DW2 inhibitor (FIG. 5C). Although the fluorine substitution on the pyridine moiety of the pyridocarbazole does not make direct interactions with the protein, the highly electron rich fluorine could mediate long range electrostatic interactions with the highly polar proximal surface of the inhibitor binding cavity formed by side chains Lys833, Asp964, Asp950, Lys808, Asp836 and Lys807. The dihydroxy-t-butyl (DHtB) group on the amide linkage of the Cp ring sticks into the space sandwiched by the main chain carbonyl and side chain of Ala805 as well as the side chain of Lys890. This places the two hydroxyl groups of the DHtB moiety in a favorable position to form hydrogen bonding interactions with several main chain and side chain atoms in this region, although the electron density map corresponding to the DHtB moiety is not well enough defined to assign details of the interaction. The close van der Waals surface complementarity between the derivatized DHtB group and the adjacent protein also facilitates binding. Moreover, the polar nature of the DHtB group on the rather hydrophobic Cp ring ligand also likely makes more complimentary interactions with the solvent channel into the inhibitor binding pocket relative to the underivatized Cp ring.

An interesting feature of the PI3Kγ complex with E5E2 relative to its complex with the DW2 inhibitor is the alkyl (methyl) derivatization on the maleimide moiety, which only slightly increases inhibitory potency but significantly increases binding selectivity (FIG. 2C). In the PI3Kγ/E5E2 structure this methyl group on the maleimide nitrogen is within van der Waals contact distance with a tyrosine residue (Tyr867) that is conserved among Class I PI3K enzymes but not present in protein kinases. Therefore, the methyl group of the E5E2 inhibitor is well accommodated in this pocket backed by Tyr867 of PI3Kγ, which is in contrast to the limited space present in the same region of organometallic inhibitors complex structures with protein kinases such as GSK3 and PIM1. Taken together, this analysis suggests that the maleimide methyl group of E5E2 inhibitor might be a particularly important kinase inhibitor specificity determinant of this inhibitor.

Figure 6A:
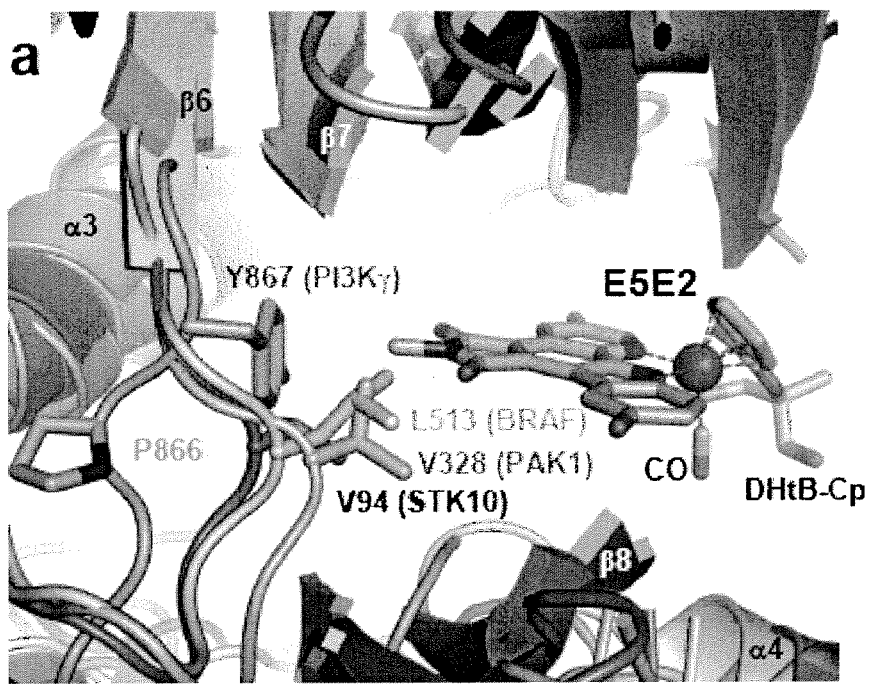
FIG. 6 provides structural comparisons of PI3Kγ/E5E2 with other protein kinases.

Structural basis of PI3K specificity of the E5E2 inhibitor. An overlay of the PI3Kγ/E5E2 structure with several other kinase structures in addition to GSK3 and PIM1 including BRAF, STK10 (shares more than 65% sequence homology with MST1) and PAK1 reveals that while each of the kinases share a high degree of structural homology within the inhibitor binding site, there is significant difference in the Tyr867-bearing loop preceding the β6 strand. In particular, Pro866 of PI3Kγ faces away from the methylated maleimide of E5E2, while the corresponding hydrophobic residues of the other kinases are in a position that would clash with the methyl group on the maleimide of the inhibitor (FIG. 6A). This modeling is consistent with the poor inhibitory properties of E5E2 for these other kinases.

Figure 6B:
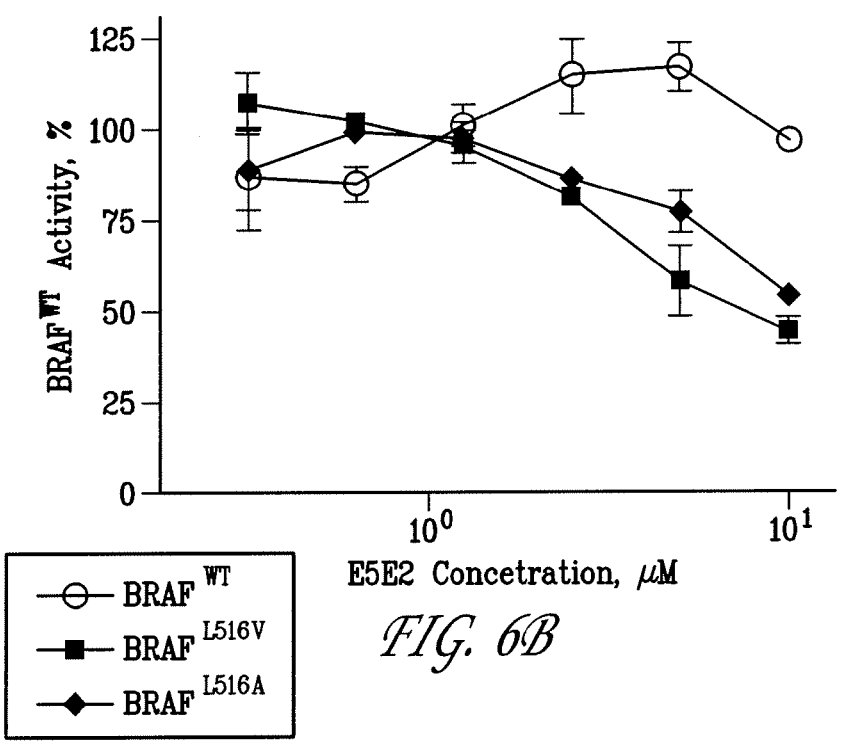

Based on the observations described above, it was hypothesized that Tyr867 and Pro866 mediate important roles in the PI3K selectivity of the E5E2 inhibitor. To test this hypothesis, a site directed mutagenesis of the BRAF kinase was carried out, directed at increasing its sensitivity to the E5E2 inhibitor. Specifically, Leu513 of BRAF (analogous to Tyr867 of PI3Kγ) was mutated to the less bulky valine and alanine residues and compared the ability of these mutants to be inhibited by the E5E2 inhibitor. Consistent with the hypothesis, the E5E2 inhibitor shows an IC50 of about 10 μM for the BRAF mutants, while the E5E2 inhibitor shows no detectable inhibition against wild-type BRAF at an inhibitor concentration of 10 μM (FIG. 6B). Taken together, these results suggest that the specific alkylation (methylation) on E5E2 inhibitor complements with a unique conformation centered around Tyr867 on PI3Kγ to mediate selective inhibition against PI3K lipid kinases over protein kinases. Furthermore, E5E2 also serves as an excellent lead compound for the further development of potent and specific organoruthenium PI3K inhibitors.

A molecular switch controlling organometallic inhibitor selectivity for lipid kinases. The use of a pyridocarbazole organometallic scaffold as a template for designing protein kinase inhibitors arose from a chemical mimetic strategy based on the property of staurosporine as a nonselective kinase inhibitor and the versatility of ligand shuffling around the metal for specificity towards the intricate differences in kinase ATP binding pockets. A close examination of protein kinase structures in complex with staurosporine revealed a strikingly unified feature of two invariant direct hydrogen bonding interactions between the lactam moiety of staurosporine and the protein. The lactam moiety of staurosporine is exploited and converted into a maleimide moiety in the original design of the initial inhibitor derived from an organometallic scaffold to confer inhibitory potency. Structural studies centering on this new class of highly specific organoruthenium inhibitors, particularly in complex with two representative protein kinases GSK3 (unpublished data) and PIM1 (21), have confirmed that the two invariant hydrogen bonds are largely conserved in the binding of organoruthenium inhibitor in the protein kinase pocket. In the follow-up studies, it was discovered that a methyl group addition to the maleimide moiety nearly abolished the inhibitory activity. From the structural point of view, this is reasonably anticipated because a methyl group would disrupt the hydrogen bonding interactions mediated by the maleimide imide as well as introduce additional steric clashes with the protein.

Despite the overall structural homology of PI3K lipid kinases with protein kinases, its mode of staurosporine binding is quite divergent. In particular, the direct hydrogen bonding interactions described above for protein kinases are not present in PI3Kγ. This observation is mirrored in the structure of PI3Kγ bound to the organoruthenium DW2 inhibitor. This feature was adapted by adding a methyl group on the maleimide imide (compound E5E2 and DW12Me) to occupy this space. As expected, these inhibitors were potent for PI3K but not for several protein kinases. From the structural analysis of the complex between PI3Kγ and the E5E2 inhibitor, a Tyr867 residue that plays a central role in accommodating the methylated imide was identified, and the structural basis for why protein kinases cannot accommodate the methylated imide was modeled. This modeling was tested by producing a site directed mutant of the BRAF protein kinases that re-sensitizes it to the E5E2 inhibitor. The results highlight the importance of this alkyl (methyl) group on the maleimide moiety of the presently-disclosed class of organoruthenium inhibitor as a selectivity switch between PI3K lipid kinases and protein kinases.

Figure 10A:
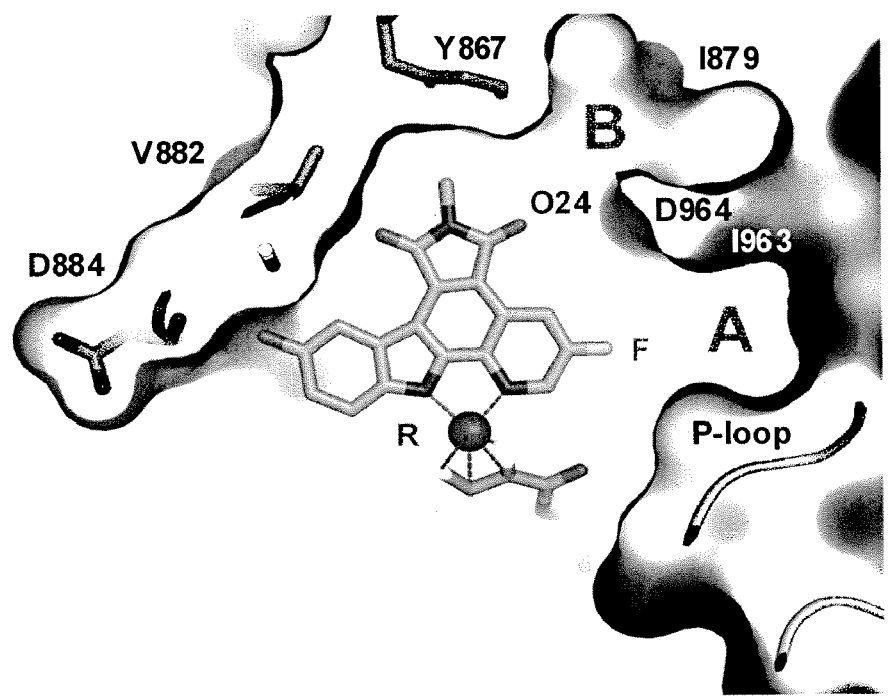
FIG. 10 illustrates a study designed to examine the structure of additional organoruthenium kinase inhibitors.
Figure 10B:
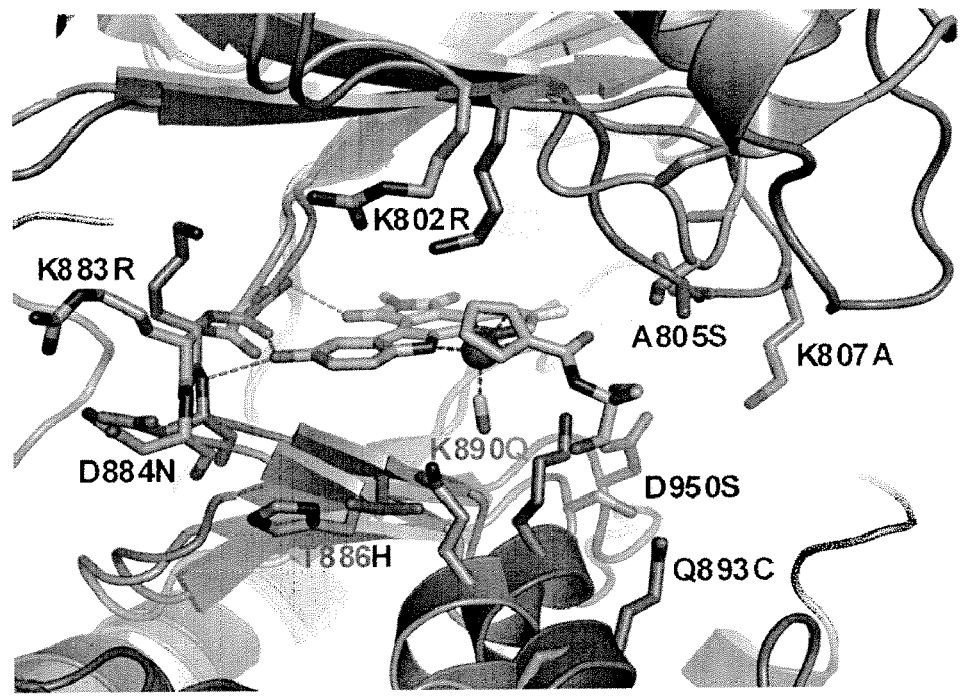
Figure 10C:
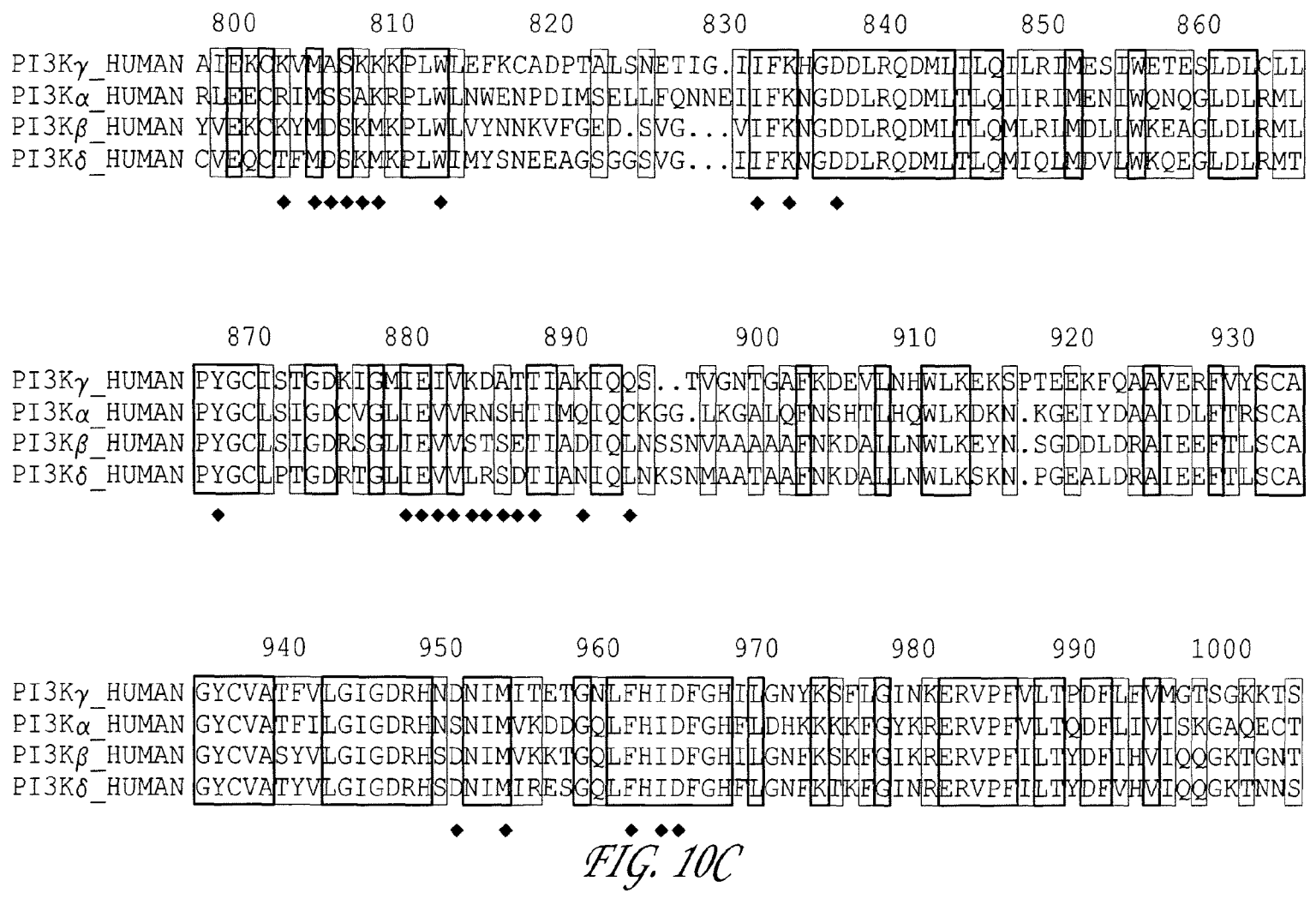
Figure 10D:
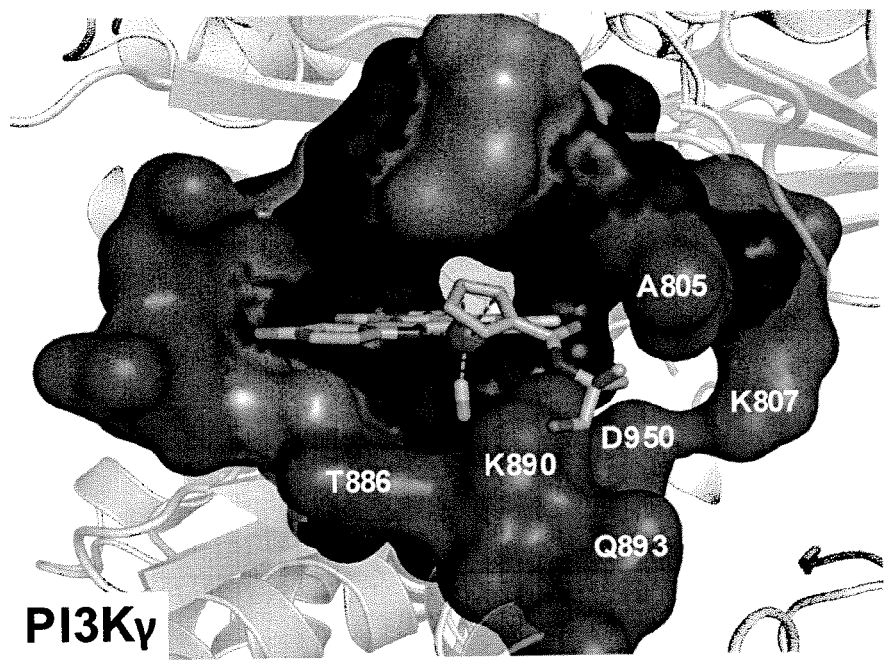
Figure 10E:
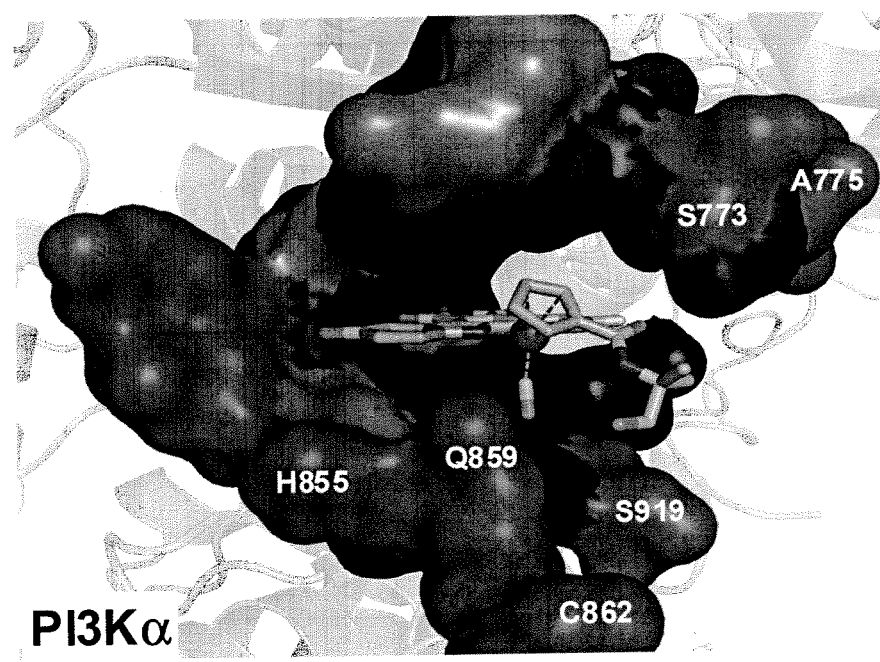

Design of improved PI3K inhibitors using an organoruthenium scaffold. FIG. 10 illustrates a study designed to examine the structure of additional organoruthenium kinase inhibitors. FIG. 10A shows a sliced surface representation of the E5E2 inhibitor bound to PI3Kγ along the plane of the E5E2 aromatic rings. Residues of the hinge region between the N-lobe and C-lobe are labeled. The B pocket is gated by residues I879, D964, Y867 and I963. E5E2 atoms are labeled according to PDB coordinate assignment. FIG. 10B shows a superimposition of E5E2 bound PI3Kγ with PI3Kα (Huang, C. H., Mandelker, D., Schmidt-Kittler, O., Samuels, Y., Velculescu, V. E., Kinzler, K. W., Vogelstein, B., Gabelli, S. B., and Amzel, L. M. (2007) *The structure of a human p110alpha/p85alpha complex elucidates the effects of oncogenic PI3Kalpha mutations*, Science 318, 1744-1748) (PDB: 2RD0). PI3Kγ and PI3Kα cartoons are shown in blue and red, respectively and highlighted residues are shown as sticks with only the variable residues shown. Residue numbering is for PI3Kγ and labels represent the homologous position from sequence alignment. FIG. 10C shows a sequence alignment of PI3Kα, β, δ, γ isoforms kinase domains (ESPript 2.2; Gouet, P., Robert, X, and Courcelle, E. (2003) *ESPript/ENDscript: Extracting and rendering sequence and 3D information from atomic structures of proteins*, Nucleic Acids Res 31, 3320-3323). Colored diamonds represent the residues within 5 Å contact radius with E5E2 in the PI3Kγ co-crystal structure. Strictly conserved residues among PI3K isoforms are shown in blue, conserved residues are shown in light blue and variable residues are shown in magenta, according to the sequence alignment of PI3Kα, β, δ, γ kinase domains. The color-coding scheme for sequence conservation is preserved in FIGS. 10D and 10E. In FIGS. 10D and 10E, provided are surface representations of residues within 5 Å of E5E2 in the E5E2-PI3Kγ (FIG. 10D) and homologous residues on the PI3Kα structure (FIG. 10E). E5E2 was modeled by superimposing PI3Kγ/E5E2 complex structure with unliganded PI3Kα structure. The most variable residues between PI3Kγ and PI3Kα are annotated on the surface representation of the structure.

The present study has identified mid-low nanomolar organoruthenium with significant selectivity towards PI3K, yet other structural aspects of the present study can still be used as a guide to further improve PI3K potency and isoform selectivity.

First, the fluorine atom of the pyridocarbazole ring faces the A pocket in the PI3K active site that would better accommodate a larger R group that could mediate direct hydrogen bonds. Thus, any R group bearing a moiety that features an electronegative atom or an electronegative atom bound to a hydrogen may constitute a substituent on the pyridocarbazole ring. Those skilled in the art may readily identify examples of such R groups and moieties. Nonlimiting examples include alcohols, amine groups, chloroform, trifluoroalkyl, carbonyl, and the like.

Second, a shallower pocket proximal to a maleimide carbonyl group (B pocket) formed by residues Asp964, Ile963, Tyr867 and Ile879 should accommodate a larger R group than the methyl substituent on the maleimide nitrogen (FIG. 10A). For example, substituents may include $C_1$-$C_6$ straight or branched chain alkyl or alkenyl, optionally substituted with halo, hydroxyl, nitro, trifluoromethyl, $C_1$-$C_6$ straight or branched chain alkyl or alkenyl, $C_1$-$C_4$ alkoxy, $C_1$-$C_4$ alkenyloxy, phenoxy, benzyloxy, or amino.

Both modifications are likely to increase PI3K potency and specificity. When overlaid with the recently published PI3Kα crystal structure (34), the E5E2 inhibitor of the PI3Kγ/E5E2 structure would be predicted to make analogous interactions with PI3Kα. Nearly 70% of the residues of PI3Kγ that make van der Waals contacts with the E5E2 inhibitor are conserved both in sequence and structure in PI3Kα (FIGS. 10B, C). This observation is consistent with the finding that the PI3Kγ and α isoforms are close "pharmologues" exemplified by their similarity for their sensitivity to isoform specific PI3K inhibitors (28). However, there are regions of divergence directly outside the E5E2 binding site that might be exploited for the design of organoruthenium inhibitors with PI3K isoform selectivity (FIGS. 10C, D, and E). In particular, the variations in the solvent exposed region of the ATP binding pocket provide an opportunity to identify a Cp derivatization that might distinguish between PI3K isoforms.

Taken together, the present study has identified a new class of mid-low nanomolar organoruthenium inhibitors against PI3Kγ that also show significant selectivity against other protein kinase families. Crystallographic analysis of these inhibitors bound to PI3Kγ reveals the mechanism of inhibition and identifies a structural switch that confers significant selectivity against PI3Ks over protein kinases. The disclosed structural analysis also suggests further modifications to increase PI3K potency and PI3K isoform selectivity.

Experimental Methods.

Protein Expression and Purification. Baculovirus harboring the human PI3K p110γ catalytic subunit construct spanning amino acid sequence 144-1202 (ΔPI3Kγ) was obtained from the MRC, United Kingdom. ΔPI3Kγ protein was expressed essentially as previously described (26, 35) with minor modifications. ΔPI3Kγ was concentrated to 6 mg/mL as measured using a Bradford protein assay and frozen for storage.

Crystallization, Inhibitor Soaking, and Data Collection. Initial crystals of ΔPI3Kγ were obtained using hanging drop vapor diffusion by mixing 1 μL of ΔPI3Kγ protein (6 mg/mL) with 1 μL of crystallization solution (100 mM Tris pH 7.2, 200 mM Ammonium sulfate, 21% PEG 4000). Diffraction quality crystals grew under streak seeding using initial crystals as seeds with a reduced percentage of PEG 4000 (15-18%). After seeding, crystals reached maximum size in two weeks and were subjected to soaking with inhibitor dissolved in cryoprotectant (100 mM Tris pH 7.2, 200 mM ammonium sulfate, 25% PEG 4000, 15% Glycerol) with a concentration gradient of inhibitor from 1 μM to 1 mM in 10-fold gradations. Crystals were incubated with a final inhibitor concentration of 1 mM in cryoprotectant for 4 hours to overnight and finally flash frozen in liquid propane. Diffraction images were collected at 100 K using a MARCCD 300 detector at APS beamline 23ID-D (Argonne National Laboratory) or at NSLS beamline X6A (Brookhaven National Laboratory). Diffraction images were indexed, integrated and scaled using the HKL2000 package (HKL Research). Scaled data were processed with the CCP4 suite (36). The space group was determined to be C2 and each asymmetric unit contains one molecule.

Structural Determination and Refinement. ΔPI3Kγ inhibitor complex structures were solved by molecular replacement using MolRep (37) with the human unliganded PI3K structure (PDB accession code: 1E8Y) as the search model. The initial solution was refined by rigid body, simulated annealing, torsion angle dynamic, and B factor refinements using CNS (38), interspersed by manual adjustment of the protein model using Coot (39) and O (40). CNS parameter and topology files for organoruthenium inhibitors were generated utilizing the HIC-UP XDICT server and the inhibitor models were manually placed into the electron density from the calculated Fo-Fc map and were adjusted in Coot. This was followed by additional refinement using CNS and the final model was checked for errors by using the CNS composite omit map for protein models and simulated annealing omit map for organoruthenium inhibitors. All structural graphics are generated in PyMol (DeLano Scientific LLC).

Biochemical In Vitro Assays. PI3K fluorescence polarization kinase assay—This assay was purchased from Echelon Biosciences and was carried out for PI3Kα (p110α/p85α, Upstate) essential as recommended by the manufacturer. The final concentration of PtdIns(4,5)P2, detector and red fluorescent probe was 10 μM, 125 nM, and 10 nM respectively. PI3Kα used for each reaction was 60 pmols. The reaction was carried out in 5 mM HEPES pH 7.0, 25 mM MgCl2 and 250 μM ATP in 0.5 mM eppendorf tubes. Organometallic inhibitors were added from 4× stock solutions in 20% DMSO in reaction buffer. The final concentration of the inhibitors was 1 or 3 μM in 5% DMSO. PI3Kα, PtdIns(4,5)P2, and different inhibitors were incubated for 15 min followed by the addition of MgCl2 and ATP. The reaction mixture (15 μL) was incubated for 1 hour and 10 μL of the mixtures was transferred into a 384 well-plate. To each well, 10 μL of PtdIns(3,4,5)P3 detector was added followed by the addition of 5 μL red fluorescent probe. Afterwards, fluorescent polarization was measured using and EnVision MultiLabel plate reader from PerkinElmer with appropriate filters (550 nm excitation/580 nm polarization emission). As controls, solutions with no inhibitor (100% enzyme activity) or 300 nM wortamannin (a known PI3Kα inhibitor that inhibits the kinase completely at 300 nM) were prepared. In order to investigate the potency of the inhibitors, mP values for different inhibitor containing solutions (with 3 or 1 μM inhibitor) were compared with the theoretical mP values that would be obtained when 50% of the kinase is inhibited. This value was calculated using the equation (mP(100% enzyme activity)−mP(0% enzyme activity))/2 following by a background correction.

PI3K Kinase-Glo Assay. Recombinantly expressed human PI3Kγ catalytic domain was preincubated with various concentration of inhibitors with a final DMSO concentration of 2% in reaction buffer (20 mM Tris pH 7.5, 100 mM NaCl, 10 mM MgCl2) for 1 hour at room temperature before this mixture was added to a solution of 0.1 mg/mL D-myo-Phosphatidylinositol 4,5-biphosphate (PtdIns (4,5)P2, Echelon Biosciences) and 10 μM ATP. 14 pmoles PI3K was used in compounds DW12, DW12Me, EAd125 comparison and 1.4 pmoles PI3K was used for compounds E5, E5E2, E5E1 measurements. The kinase reaction was carried out in a 50 μL final volume in a 96-well microtiter plate at 37° C. for 3 hours before 50 μL Kinase-Glo® (Promega) developing solution was added into the mixture to generate a luminescence signal. The signal was recorded using the PerkinElmer Wallac 1420 luminometer using a luminescence filter. Data were processed and IC50 values were derived from using 2% DMSO and with no kinase as controls and a sigmoidal dose response curve fitting by GraphPad Prism.

Cell Proliferation (MTT) Assay. Cells were plated into a 96-well plate at a density of $2.5 \times 10^4$ cells per ml and left to grow overnight. Cells were treated with increasing concentrations of E5E1 (0.03-30 μM), E5E1 (0.03-30 μM) or LY 294002 (Calbiochem, San Diego, Calif.) (0.01-30 μM) in triplicate. In each instance cells were grown for 72 hours before being treated with 20 μl of MTT for 3 hours (Sigma). After this time, the media was rapidly removed and the MTT crystals were solubilized using DMSO. The resulting absorbance was read in a plate reader at 560 nm. Absorbance readings were subtracted from the value of blank wells, the reduction in cell growth was calculated as a percentage of control absorbance in the absence of any drug. Data shows the mean of at least three independent experiments ± the s.e. mean.

Western Blot Analysis. Proteins were extracted and blotted for as described in (41). After analysis, Western blots were stripped once and re-probed for β-actin to demonstrate even protein loading. Antibodies to phospho-AKT and total AKT were from Cell Signaling Technology, (Beverly, Mass.). The monoclonal antibody to β-actin was from Sigma.

3D Spheroid Growth. Melanoma spheroids were prepared using the liquid overlay method. Briefly, 200 μg of melanoma cells (25,000 cells per ml) were added to a 96-well plate coated with 1.5% agar (Difco, Sparks MD). Plates were left to incubate for 72 hours, by which time cells had organized into 3D spheroids. Spheroids were then harvested using a P1000 pipette. The media was removed and the spheroids were implanted into a gel of bovine collagen I containing EMEM, L-glutamine and 2% FBS. Normal 2% melanoma media was overlaid on top of the solidified collagen. Spheroids were treated with either E5E1 (10-30 μM), or E5E2 (10-30 μM), before being left to grow for 72 hours. Spheroids were then washed twice in PBS before being treated with calcein-AM, ethidium bromide (Molecular Probes, Eugene, Oreg.) for 1 hour at 37° C., according to the manufacturer's instruction. After this time, pictures of the invading spheroids were taken using a Nikon-300 inverted fluorescence microscope.

REFERENCES

1. Fruman, D. A., Meyers, R. E., and Cantley, L. C. (1998) Phosphoinositide kinases, *Annu Rev Biochem* 67, 481-507.
2. Vanhaesebroeck, B., and Waterfield, M. D. (1999) Signaling by distinct classes of phosphoinositide 3-kinases, *Exp Cell Res* 253, 239-254.
3. Domin, J., and Waterfield, M. D. (1997) Using structure to define the function of phosphoinositide 3-kinase family members, *FEBS Lett* 410, 91-95.
4. Rodriguez-Viciana, P., Warne, P. H., Dhand, R., Vanhaesebroeck, B., Gout, I., Fry, M. J., Waterfield, M. D., and Downward, J. (1994) Phosphatidylinositol-3-OH kinase as a direct target of Ras, *Nature* 370, 527-532.
5. Vivanco, I., and Sawyers, C. L. (2002) The phosphatidylinositol 3-Kinase AKT pathway in human cancer, *Nat Rev Cancer* 2, 489-501.
6. Whitman, M., Kaplan, D. R., Schaffhausen, B., Cantley, L., and Roberts, T. M. (1985) Association of phosphatidylinositol kinase activity with polyoma middle-T competent for transformation, *Nature* 315, 239-242.
7. Sugimoto, Y., Whitman, M., Cantley, L. C., and Erikson, R. L. (1984) Evidence that the Rous sarcoma virus transforming gene product phosphorylates phosphatidylinositol and diacylglycerol, *Proc Natl Acad Sci USA* 81, 2117-2121.
8. Samuels, Y., Diaz, L. A., Jr., Schmidt-Kittler, O., Cummins, J. M., Delong, L., Cheong, I., Rago, C., Huso, D. L., Lengauer, C., Kinzler, K. W., Vogelstein, B., and Velculescu, V. E. (2005) Mutant PIK3CA promotes cell growth and invasion of human cancer cells, *Cancer Cell* 7, 561-573.
9. Samuels, Y., Wang, Z., Bardelli, A., Silliman, N., Ptak, J., Szabo, S., Yan, H., Gazdar, A., Powell, S. M., Riggins, G. J., Willson, J. K., Markowitz, S., Kinzler, K. W., Vogelstein, B., and Velculescu, V. E. (2004) High frequency of mutations of the PIK3CA gene in human cancers, *Science* 304, 554.
10. Vogt, P. K., Kang, S., Elsliger, M. A., and Gymnopoulos, M. (2007) Cancer-specific mutations in phosphatidylinositol 3-kinase, *Trends Biochem Sci* 32, 342-349.
11. Benistant, C., Chapuis, H., and Roche, S. (2000) A specific function for phosphatidylinositol 3-kinase alpha (p85alpha-p110alpha) in cell survival and for phosphatidylinositol 3-kinase beta (p85alpha-p110beta) in de novo DNA synthesis of human colon carcinoma cells, *Oncogene* 19, 5083-5090.
12. Mizoguchi, M., Nutt, C. L., Mohapatra, G., and Louis, D. N. (2004) Genetic alterations of phosphoinositide 3-kinase subunit genes in human glioblastomas, *Brain Pathol* 14, 372-377.
13. Hickey, F. B., and Cotter, T. G. (2006) BCR-ABL regulates phosphatidylinositol 3-kinase-p110gamma transcription and activation and is required for proliferation and drug resistance, *J Biol Chem* 281, 2441-2450.
14. Rommel, C., Camps, M., and Ji, H. (2007) PI3K delta and PI3K gamma: partners in crime in inflammation in rheumatoid arthritis and beyond?, *Nat Rev Immunol* 7, 191-201.
15. Davies, S. P., Reddy, H., Caivano, M., and Cohen, P. (2000) Specificity and mechanism of action of some commonly used protein kinase inhibitors, *Biochem J* 351, 95-105.
16. Baggiolini, M., Dewald, B., Schnyder, J., Ruch, W., Cooper, P. H., and Payne, T. G. (1987) Inhibition of the phagocytosis-induced respiratory burst by the fungal metabolite wortmannin and some analogues, *Exp Cell Res* 169, 408-418.

17. Vlahos, C. J., Matter, W. F., Hui, K. Y., and Brown, R. F. (1994) A specific inhibitor of phosphatidylinositol 3-kinase, 2-(4-morpholinyl)-8-phenyl-4H-1-benzopyran-4-one (LY294002), *J Biol Chem* 269, 5241-5248.
18. Jacobs, M. D., Black, J., Futer, O., Swenson, L., Hare, B., Fleming, M., and Saxena, K. (2005) Pim-1 ligand-bound structures reveal the mechanism of serine/threonine kinase inhibition by LY294002, *J Biol Chem* 280, 13728-13734.
19. Knight, Z. A., Chiang, G. G., Alaimo, P. J., Kenski, D. M., Ho, C. B., Coan, K., Abraham, R. T., and Shokat, K. M. (2004) Isoform-specific phosphoinositide 3-kinase inhibitors from an arylmorpholine scaffold, *Bioorg Med Chem* 12, 4749-4759.
20. Meggers, E. (2007) Exploring biologically relevant chemical space with metal complexes, *Curr Opin Chem Biol* 11, 287-292.
21. Williams, D. S., Carroll, P. J., and Meggers, E. (2007) Platinum complex as a nanomolar protein kinase inhibitor, *Inorg Chem* 46, 2944-2946.
22. Bregman, H., Carroll, P. J., and Meggers, E. (2006) Rapid access to unexplored chemical space by ligand scanning around a ruthenium center: discovery of potent and selective protein kinase inhibitors, *J Am Chem Soc* 128, 877-884.
23. Debreczeni, J. E., Bullock, A. N., Atilla, G. E., Williams, D. S., Bregman, H., Knapp, S., and Meggers, E. (2006) Ruthenium half-sandwich complexes bound to protein kinase Pim-1, *Angew Chem Int Ed Engl* 45, 1580-1585.
24. Smalley, K. S., Contractor, R., Haass, N. K., Kulp, A. N., Atilla-Gokcumen, G. E., Williams, D. S., Bregman, H., Flaherty, K. T., Soengas, M. S., Meggers, E., and Herlyn, M. (2007) An organometallic protein kinase inhibitor pharmacologically activates p53 and induces apoptosis in human melanoma cells, *Cancer Res* 67, 209-217.
25. Atilla-Gokcumen, G. E., Williams, D. S., Bregman, H., Pagano, N., and Meggers, E. (2006) Organometallic compounds with biological activity: a very selective and highly potent cellular inhibitor for glycogen synthase kinase 3, *Chembiochem* 7, 1443-1450.
26. Williams, D. S., Atilla, G. E., Bregman, H., Arzoumanian, A., Klein, P. S., and Meggers, E. (2005) Switching on a signaling pathway with an organoruthenium complex, *Angew Chem Int Ed Engl* 44, 1984-1987.
27. Bregman, H., and Meggers, E. (2006) Ruthenium half-sandwich complexes as protein kinase inhibitors: an N-succinimidyl ester for rapid derivatizations of the cyclopentadienyl moiety, *Org Lett* 8, 5465-5468.
28. Walker, E. H., Pacold, M. E., Perisic, O., Stephens, L., Hawkins, P. T., Wymann, M. P., and Williams, R. L. (2000) Structural determinants of phosphoinositide 3-kinase inhibition by wortmannin, LY294002, quercetin, myricetin, and staurosporine, *Mol Cell* 6, 909-919.
29. Camps, M., Ruckle, T., Ji, H., Ardissone, V., Rintelen, F., Shaw, J., Ferrandi, C., Chabert, C., Gillieron, C., Francon, B., Martin, T., Gretener, D., Perrin, D., Leroy, D., Vitte, P. A., Hirsch, E., Wymann, M. P., Cirillo, R., Schwarz, M. K., and Rommel, C. (2005) Blockade of PI3Kgamma suppresses joint inflammation and damage in mouse models of rheumatoid arthritis, *Nat Med* 11, 936-943.
30. Knight, Z. A., Gonzalez, B., Feldman, M. E., Zunder, E. R., Goldenberg, D. D., Williams, O., Loewith, R., Stokoe, D., Balla, A., Toth, B., Balla, T., Weiss, W. A., Williams, R. L., and Shokat, K. M. (2006) A pharmacological map of the PI3-K family defines a role for p110alpha in insulin signaling, *Cell* 125, 733-747.
31. Bregman, H., Williams, D. S., Atilla, G. E., Carroll, P. J., and Meggers, E. (2004) An organometallic inhibitor for glycogen synthase kinase 3, *J Am Chem Soc* 126, 13594-13595.
32. Meggers, E., Atilla-Gokcumen, G. E., Bregman, H., Maksimoska, J., Mulcahy, S. P., Pagano, N., and Williams, D. S. (2007) *Synlette First*.
33. Smalley, K. S., and Herlyn, M. (2005) Targeting intracellular signaling pathways as a novel strategy in melanoma therapeutics, *Ann N Y Acad Sci* 1059, 16-25.
34. Stahl, J. M., Sharma, A., Cheung, M., Zimmerman, M., Cheng, J. Q., Bosenberg, M. W., Kester, M., Sandirasegarane, L., and Robertson, G. P. (2004) Deregulated Akt3 activity promotes development of malignant melanoma, *Cancer Res* 64, 7002-7010.
35. Smalley, K. S., Haass, N. K., Brafford, P. A., Lioni, M., Flaherty, K. T., and Herlyn, M. (2006) Multiple signaling pathways must be targeted to overcome drug resistance in cell lines derived from melanoma metastases, *Mol Cancer Ther* 5, 1136-1144.
36. Huang, C. H., Mandelker, D., Schmidt-Kittler, O., Samuels, Y., Velculescu, V. E., Kinzler, K. W., Vogelstein, B., Gabelli, S. B., and Amzel, L. M. (2007) The structure of a human p110alpha/p85alpha complex elucidates the effects of oncogenic PI3Kalpha mutations, *Science* 318, 1744-1748.
37. Walker, E. H., Perisic, O., Ried, C., Stephens, L., and Williams, R. L. (1999) Structural insights into phosphoinositide 3-kinase catalysis and signaling, *Nature* 402, 313-320.
38. Collaborative Computational Project, N. (1994) The CCP4 suite: programs for protein crystallography, *Acta Crystallogr D Biol Crystallogr* 50, 760-763.
39. Vagin, A., and Teplyakov, A. (1997) MOLREP: an automated program for molecular replacement, *J Appl Cryst* 30, 1022-1025.
40. Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T., and Warren, G. L. (1998) Crystallography & NMR system: A new software suite for macromolecular structure determination, *Acta Crystallogr D Biol Crystallogr* 54, 905-921.
41. Emsley, P., and Cowtan, K. (2004) Coot: Model-Building Tools for Molecular Graphics, *Acta Crystallogr. D* 60, 2126-2132.
42. Jones, T. A., Zou, J. Y., Cowan, S. W., and Kjeldgaard, M. (1991) Improved methods for building protein models in electron density maps and the location of errors in these models, *Acta Crystallogr. A* 47, 110-119.
43. Krissinel, E., and Henrick, K. (2004) Secondary-structure matching (SSM), a new tool for fast protein structure alignment in three dimensions, *Acta Crystallogr D Biol Crystallogr* 60, 2256-2268.
44. Smalley, K. S. M., Brafford, P., Haass, N. K., Brandner, J. M., Brown, E., and Herlyn, M. (2005) Up-regulated expression of zonula occludens protein-1 in human melanoma associates with N-cadherin and contributes to invasion and adhesion, *American Journal of Pathology* 166, 1541-1554.

What is claimed is:

1. A compound of formula I

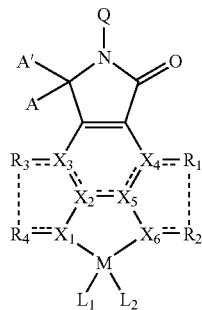

(I)

or a pharmaceutically acceptable salt thereof, wherein:

$X_1$, $X_2$, $X_3$, $X_4$, $X_5$, and $X_6$ are each independently N, C, S, O, B, or Si;

$R_1$ and $R_2$ are taken together to form a mono-, bi- or tricyclic, carbo- or heterocyclic ring, wherein the ring is either unsubstituted or substituted in one or more position(s) with halo, hydroxyl, carbonyl, nitro, amino, trihaloalkyl, substituted or unsubstituted $C_1$-$C_4$ alkoxy, substituted or unsubstituted straight or branched $C_1$-$C_6$ alkyl-OH, substituted or unsubstituted straight or branched $C_1$-$C_6$ alkyl-$NH_2$, $C_1$-$C_4$ alkenyloxy, aryl, aralkyl, phenoxy, benzyloxy, or any other hydrogen bond donor or acceptor, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S;

$R_3$ and $R_4$ are taken together to form a mono-, bi- or tricyclic, carbo-, or heterocyclic ring, wherein the ring is either unsubstituted or substituted in one or more position(s) with halo, hydroxyl, carbonyl, nitro, amino, trihaloalkyl, substituted or unsubstituted $C_1$-$C_4$ alkoxy, substituted or unsubstituted straight or branched $C_1$-$C_6$ alkyl-OH, substituted or unsubstituted straight or branched $C_1$-$C_6$ alkyl-$NH_2$, $C_1$-$C_4$ alkenyloxy, aryl, aralkyl, phenoxy, benzyloxy, or any other hydrogen bond donor or acceptor, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S;

M is Ru, Pt, Tc, Re, Os, Rh, Ir, Pd, Au, Cu, Fe, Co, or Cr;

Q is straight or branched chain $C_1$-$C_6$ alkyl or alkenyl, optionally substituted with halo, hydroxyl, nitro, trifluoromethyl, $C_1$-$C_4$ straight or branched chain alkyl or alkenyl, $C_1$-$C_4$ alkoxy, $C_1$-$C_4$ alkenyloxy, phenoxy, benzyloxy, or amino;

A and A' are each independently hydrogen, hydroxy, hydroxymethyl, $C_1$-$C_6$ straight or branched chain alkyl, $C_2$-$C_6$ straight or branched chain alkenyl, O—($C_1$-$C_6$ straight or branched chain alkyl), or O—($C_2$-$C_6$ straight or branched chain alkenyl), or A and A' are taken together as =O;

$L_1$ is a monodentate ligand capable of acting as a ligand for said metal M, a bidentate ligand capable of acting as a ligand for said metal M, or a tridentate ligand capable of acting as a ligand for said metal M; and, $L_2$ is cyclopentadienylamido.

2. The compound according to claim 1 wherein $L_1$ is selected from the group consisting of halo, hydroxy, carbonyl, amine, nitro, sulfhydryl, pyridine, thiolate, histidine, methionine, cysteine, dimethylsulfoxide, substituted or unsubstituted pyridines, substituted or unsubstituted amines, substituted or unsubstituted diamines, substituted or unsubstituted thiols, substituted or unsubstituted dithiols, substituted or unsubstituted imidazoles, substituted or unsubstituted pyrazoles, substituted or unsubstituted benzimidazoles, substituted or unsubstituted 1,4-dienes, substituted or unsubstituted 2-(aminomethyl)pyridines, substituted or unsubstituted 2-iminopyridines, substituted bipyridines, substituted or unsubstituted phenanthrolines, substituted or unsubstituted 8-hydroxyquinolines, substituted or unsubstituted 6-mercaptopurines, and substituted or unsubstituted phosphines.

3. The compound according to claim 1, wherein said $X_1$, $X_2$, $X_3$, $X_4$, $X_5$, and $X_6$ are each independently selected from the group consisting of N and C.

4. The compound according to claim 1, wherein said M is Ru or Pt.

5. The compound according to claim 1, wherein said $R_1$ and $R_2$ are taken together to form a monocyclic 5 or 6 membered ring, or a bicyclic indene, indene derivative, naphthalene, or naphthalene derivative ring, and wherein said ring is carbocyclic or heterocyclic.

6. The compound according to claim 1, wherein said $R_3$ and $R_4$ are taken together to form a monocyclic 5 or 6 membered ring, or a bicyclic indene, indene derivative, naphthalene, or naphthalene derivative ring, and wherein said ring is carbocyclic or heterocyclic.

7. The compound according to claim 1, wherein said compound is of formula II

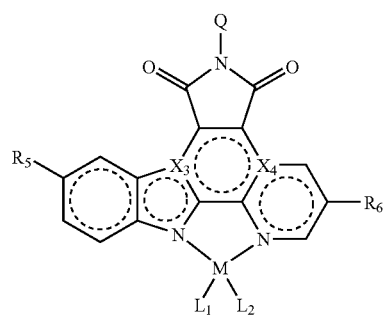

(II)

or a pharmaceutically acceptable salt thereof, wherein:

$X_3$ and $X_4$ are each independently N or C;

$R_5$ is halo, hydroxyl, carbonyl, nitro, amino, $C_1$-$C_4$ alkoxy, $C_1$-$C_4$ alkyl-OH, $C_1$-$C_4$ alkyl-OH, $NH_2$, $C_1$-$C_4$ alkenyloxy, aryl, aralkyl, phenoxy, or benzyloxy;

$R_6$ is fluoro, hydroxyl, amino, trifluoroalkyl, chloroform, substituted or unsubstituted $C_1$-$C_6$ straight or branched alkyl-OH, substituted or unsubstituted $C_1$-$C_6$ straight or branched alkyl-$NH_2$, or any other hydrogen bond donor or acceptor; and, M is Ru or Pt.

8. The compound according to claim 7, wherein said compound is of formula III (III)

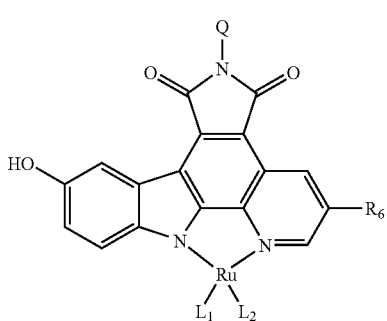

or a pharmaceutically acceptable salt thereof.

9. The compound according to claim 8 wherein:
   $L_1$ is —C≡O$^+$.

10. The compound according to claim 8 wherein $R_6$ is fluorine.

11. The compound according to claim 8 wherein Q is methyl.

12. The compound according to claim 8 wherein said compound is of formula IV (IV)

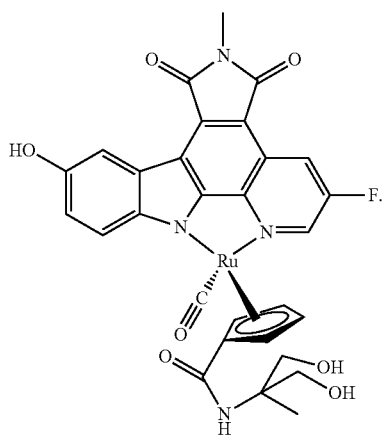

13. A pharmaceutical composition comprising a compound of formula I (I)

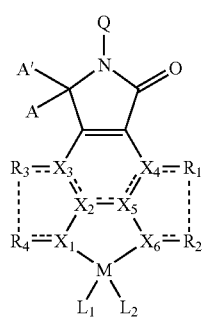

or a pharmaceutically acceptable salt thereof, wherein:
   $X_1, X_2, X_3, X_4, X_5$, and $X_6$ are each independently N, C, S, O, B, or Si;
   $R_1$ and $R_2$ are taken together to form a mono-, bi- or tricyclic, carbo- or heterocyclic ring, wherein the ring is either unsubstituted or substituted in one or more position(s) with halo, hydroxyl, carbonyl, nitro, amino, trihaloalkyl, substituted or unsubstituted $C_1$-$C_4$ alkoxy, substituted or unsubstituted straight or branched $C_1$-$C_6$ alkyl-OH, substituted or unsubstituted straight or branched $C_1$-$C_6$ alkyl-NH$_2$, $C_1$-$C_4$ alkenyloxy, aryl, aralkyl, phenoxy, benzyloxy, or any other hydrogen bond donor or acceptor, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S;
   $R_3$ and $R_4$ are taken together to form a mono-, bi- or tricyclic, carbo-, or heterocyclic ring, wherein the ring is either unsubstituted or substituted in one or more position(s) with halo, hydroxyl, carbonyl, nitro, amino, trihaloalkyl, substituted or unsubstituted $C_1$-$C_4$ alkoxy, substituted or unsubstituted straight or branched $C_1$-$C_6$ alkyl-OH, substituted or unsubstituted straight or branched $C_1$-$C_6$ alkyl-NH$_2$, $C_1$-$C_4$ alkenyloxy, aryl, aralkyl, phenoxy, benzyloxy, or any other hydrogen bond donor or acceptor, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S;
   M is Ru, Pt, Tc, Re, Os, Rh, Ir, Pd, Au, Cu, Fe, Co, or Cr;
   Q is straight or branched chain $C_1$-$C_6$ alkyl or alkenyl, optionally substituted with halo, hydroxyl, nitro, trifluoromethyl, $C_1$-$C_4$ straight or branched chain alkyl or alkenyl, $C_1$-$C_4$ alkoxy, $C_1$-$C_4$ alkenyloxy, phenoxy, benzyloxy, or amino;
   A and A' are each independently hydrogen, hydroxy, hydroxymethyl, $C_1$-$C_6$ straight or branched chain alkyl, $C_2$-$C_6$ straight or branched chain alkenyl, O—($C_1$-$C_6$ straight or branched chain alkyl), or O—($C_2$-$C_6$ straight or branched chain alkenyl), or
   A and A' are taken together as =O;
   $L_1$ is a monodentate ligand capable of acting as a ligand for said metal M, a bidentate ligand capable of acting as a ligand for said metal M, or a tridentate ligand capable of acting as a ligand for said metal M; and,
   $L_2$ is cyclopentadienylamido.

14. The pharmaceutical composition according to claim 13 comprising a compound of formula II (II)

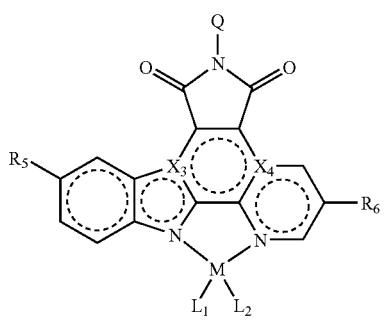

or a pharmaceutically acceptable salt thereof, wherein:
   $X_3$ and $X_4$ are each independently N or C;
   $R_5$ is halo, hydroxyl, carbonyl, nitro, amino, $C_1$-$C_4$ alkoxy, $C_1$-$C_4$ alkyl-OH, $C_1$-$C_4$ alkyl-OH, NH$_2$, $C_1$-$C_4$ alkenyloxy, aryl, aralkyl, phenoxy, or benzyloxy;

$R_6$ is fluoro, hydroxyl, amino, trifluoroalkyl, chloroform, substituted or unsubstituted $C_1$-$C_6$ straight or branched alkyl-OH, substituted or unsubstituted $C_1$-$C_6$ straight or branched alkyl-NH$_2$, or any other hydrogen bond donor or acceptor; and, M is Ru or Pt.

15. The pharmaceutical composition according to claim 14 comprising a compound of formula III

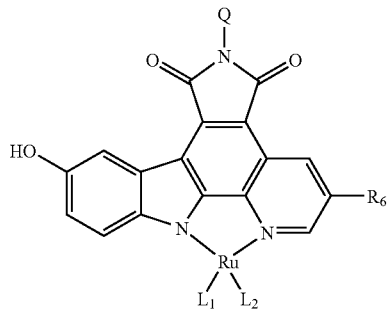

(III)

or a pharmaceutically acceptable salt thereof.

16. The pharmaceutical composition according to claim 15 wherein:

$L_1$ is —C≡O$^+$.

17. The pharmaceutical composition according to claim 15 wherein $R_6$ is fluorine.

18. The pharmaceutical composition according to claim 15 wherein Q is methyl.

19. The pharmaceutical composition according to claim 15 wherein said compound is of formula IV

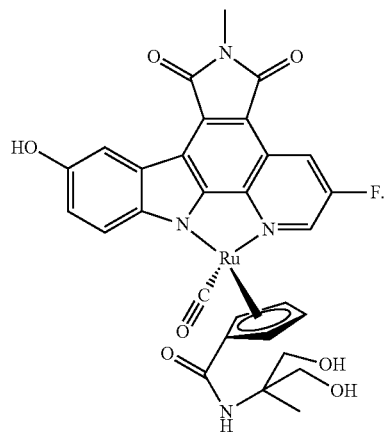

(IV)

20. A method for inhibiting melanoma cell proliferation, migration, or both comprising contacting a melanoma cell with a compound of formula I:

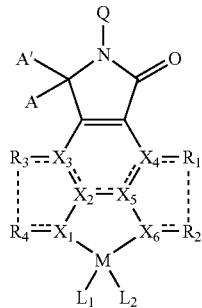

(I)

or a pharmaceutically acceptable salt thereof, wherein:

$X_1$, $X_2$, $X_3$, $X_4$, $X_5$, and $X_6$ are each independently N, C, S, O, B, or Si;

$R_1$ and $R_2$ are taken together to form a mono-, bi- or tricyclic, carbo- or heterocyclic ring, wherein the ring is either unsubstituted or substituted in one or more position(s) with halo, hydroxyl, carbonyl, nitro, amino, trihaloalkyl, substituted or unsubstituted $C_1$-$C_4$ alkoxy, substituted or unsubstituted straight or branched $C_1$-$C_6$ alkyl-OH, substituted or unsubstituted straight or branched $C_1$-$C_6$ alkyl-NH$_2$, $C_1$-$C_4$ alkenyloxy, aryl, aralkyl, phenoxy, benzyloxy, or any other hydrogen bond donor or acceptor, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S;

$R_3$ and $R_4$ are taken together to form a mono-, bi- or tricyclic, carbo-, or heterocyclic ring, wherein the ring is either unsubstituted or substituted in one or more position(s) with halo, hydroxyl, carbonyl, nitro, amino, trihaloalkyl, substituted or unsubstituted $C_1$-$C_4$ alkoxy, substituted or unsubstituted straight or branched $C_1$-$C_6$ alkyl-OH, substituted or unsubstituted straight or branched $C_1$-$C_6$ alkyl-NH$_2$, $C_1$-$C_4$ alkenyloxy, aryl, aralkyl, phenoxy, benzyloxy, or any other hydrogen bond donor or acceptor, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S;

M is Ru, Pt, Tc, Re, Os, Rh, Ir, Pd, Au, Cu, Fe, Co, or Cr;

Q is straight or branched chain $C_1$-$C_6$ alkyl or alkenyl, optionally substituted with halo, hydroxyl, nitro, trifluoromethyl, $C_1$-$C_4$ straight or branched chain alkyl or alkenyl, $C_1$-$C_4$ alkoxy, $C_1$-$C_4$ alkenyloxy, phenoxy, benzyloxy, or amino;

A and A' are each independently hydrogen, hydroxy, hydroxymethyl, $C_1$-$C_6$ straight or branched chain alkyl, $C_2$-$C_6$ straight or branched chain alkenyl, O—($C_1$-$C_6$ straight or branched chain alkyl), or O—($C_2$-$C_6$ straight or branched chain alkenyl), or A and A' are taken together as =O;

$L_1$ is a monodentate ligand capable of acting as a ligand for said metal M, a bidentate ligand capable of acting as a ligand for said metal M, or a tridentate ligand capable of acting as a ligand for said metal M; and, $L_2$ is cyclopentadienylamido.

21. A method for inhibiting PI3K or phospho-AKT kinase activity in a subject comprising administering to said subject a therapeutically effective amount of a compound of formula I

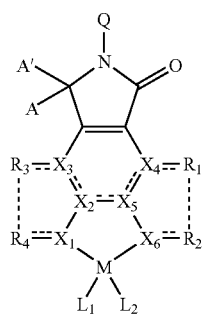

(I)

or a pharmaceutically acceptable salt thereof, wherein:

$X_1$, $X_2$, $X_3$, $X_4$, $X_5$, and $X_6$ are each independently N, C, S, O, B, or Si;

$R_1$ and $R_2$ are taken together to form a mono-, bi- or tricyclic, carbo- or heterocyclic ring, wherein the ring is either unsubstituted or substituted in one or more position(s) with halo, hydroxyl, carbonyl, nitro, amino, trihaloalkyl, substituted or unsubstituted $C_1$-$C_4$ alkoxy, substituted or unsubstituted straight or branched $C_1$-$C_6$ alkyl-OH, substituted or unsubstituted straight or branched $C_1$-$C_6$ alkyl-$NH_2$, $C_1$-$C_4$ alkenyloxy, aryl, aralkyl, phenoxy, benzyloxy, or any other hydrogen bond donor or acceptor, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S;

$R_3$ and $R_4$ are taken together to form a mono-, bi- or tricyclic, carbo-, or heterocyclic ring, wherein the ring is either unsubstituted or substituted in one or more position(s) with halo, hydroxyl, carbonyl, nitro, amino, trihaloalkyl, substituted or unsubstituted $C_1$-$C_4$ alkoxy, substituted or unsubstituted straight or branched $C_1$-$C_6$ alkyl-OH, substituted or unsubstituted straight or branched $C_1$-$C_6$ alkyl-$NH_2$, $C_1$-$C_4$ alkenyloxy, aryl, aralkyl, phenoxy, benzyloxy, or any other hydrogen bond donor or acceptor, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S;

M is Ru, Pt, Tc, Re, Os, Rh, Ir, Pd, Au, Cu, Fe, Co, or Cr;

Q is straight or branched chain $C_1$-$C_6$ alkyl or alkenyl, optionally substituted with halo, hydroxyl, nitro, trifluoromethyl, $C_1$-$C_4$ straight or branched chain alkyl or alkenyl, $C_1$-$C_4$ alkoxy, $C_1$-$C_4$ alkenyloxy, phenoxy, benzyloxy, or amino;

A and A' are each independently hydrogen, hydroxy, hydroxymethyl, $C_1$-$C_6$ straight or branched chain alkyl, $C_2$-$C_6$ straight or branched chain alkenyl, O—($C_1$-$C_6$ straight or branched chain alkyl), or O—($C_2$-$C_6$ straight or branched chain alkenyl), or A and A' are taken together as =O;

each $L_1$ is a monodentate ligand capable of acting as a ligand for said metal M, a bidentate ligand capable of acting as a ligand for said metal M, or a tridentate ligand capable of acting as a ligand for said metal M; and $L_2$ is cyclopentadienylamido.

* * * * *